US010131637B2

(12) United States Patent
Abdel-Meguid et al.

(10) Patent No.: US 10,131,637 B2
(45) Date of Patent: Nov. 20, 2018

(54) ANTI-PCSK9 COMPOUNDS AND METHODS FOR THE TREATMENT AND/OR PREVENTION OF CARDIOVASCULAR DISEASES

(71) Applicants: Shifa Biomedical Corporation, Malvern, PA (US); Temple University—of the Commonwealth System of Higher Education, Philadelphia, PA (US)

(72) Inventors: Sherin Salaheldin Abdel-Meguid, Exton, PA (US); Magid Abou-Gharbia, Exton, PA (US); Benjamin Blass, Eagleville, PA (US); Wayne Childers, New Hope, PA (US); Nabil Elshourbagy, West Chester, PA (US); Victor Ghidu, Philadelphia, PA (US); Rogelio Martinez, Trenton, NJ (US); Harold Meyers, Weston, MA (US); Shaker A. Mousa, Wynantskill, NY (US)

(73) Assignees: Shifa Biomedical Corporation, Malvern, PA (US); Temple University—Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 14/767,126

(22) PCT Filed: Mar. 11, 2014

(86) PCT No.: PCT/US2014/023135
§ 371 (c)(1),
(2) Date: Aug. 11, 2015

(87) PCT Pub. No.: WO2014/150395
PCT Pub. Date: Sep. 25, 2014

(65) Prior Publication Data
US 2015/0376139 A1 Dec. 31, 2015

Related U.S. Application Data

(60) Provisional application No. 61/789,867, filed on Mar. 15, 2013.

(51) Int. Cl.
A61K 31/4965 (2006.01)
C07D 239/42 (2006.01)
C07C 271/28 (2006.01)
C07C 275/42 (2006.01)
C07C 311/47 (2006.01)
C07C 235/38 (2006.01)
C07C 237/42 (2006.01)
(Continued)

(52) U.S. Cl.
CPC .......... *C07D 239/42* (2013.01); *A61K 31/167* (2013.01); *A61K 31/17* (2013.01); *A61K 31/18* (2013.01); *A61K 31/235* (2013.01); *A61K 31/245* (2013.01); *A61K 31/397* (2013.01); *A61K 31/40* (2013.01); *A61K 31/401* (2013.01); *A61K 31/415* (2013.01); *A61K 31/4164* (2013.01); *A61K 31/42* (2013.01); *A61K 31/435* (2013.01); *A61K 31/437* (2013.01); *A61K 31/4418* (2013.01); *A61K 31/495* (2013.01); *A61K 31/496* (2013.01); *A61K 31/505* (2013.01); *A61K 31/506* (2013.01); *C07C 235/38* (2013.01); *C07C 237/42* (2013.01); *C07C 271/28* (2013.01); *C07C 275/40* (2013.01); *C07C 275/42* (2013.01); *C07C 311/47* (2013.01); *C07D 211/14* (2013.01); *C07D 211/70* (2013.01); *C07D 211/96* (2013.01); *C07D 213/68* (2013.01); *C07D 213/74* (2013.01); *C07D 213/82* (2013.01); *C07D 231/12* (2013.01); *C07D 233/90* (2013.01); *C07D 241/04* (2013.01); *C07D 241/08* (2013.01); *C07D 261/08* (2013.01); *C07D 295/14* (2013.01); *C07D 401/06* (2013.01); *C07D 403/12* (2013.01); *C07D 471/04* (2013.01); *C07C 2601/02* (2017.05); *C07C 2601/08* (2017.05)

(58) Field of Classification Search
CPC .......................... A61K 31/495; A61K 31/505
USPC .................... 514/255.02, 275; 544/332, 383
See application file for complete search history.

(56) References Cited

U.S. PATENT DOCUMENTS 4,017,313 A 4/1977 Hartzler
4,371,607 A 2/1983 Donges
(Continued)

FOREIGN PATENT DOCUMENTS

WO 00/071508 A2 11/2000
WO 02/48099 A1 6/2002
WO WO 2012044090 * 5/2012 ........... C07D 403/12

OTHER PUBLICATIONS

Passerini, M.; Gazzetta Chimica Italiana (1921), 51(II), 181-9.*
(Continued)

Primary Examiner — Jeffrey H Murray
(74) Attorney, Agent, or Firm — Robert C. Netter, Jr.; Dann, Dorfman, Herrell and Skillman, P.C.

(57) ABSTRACT

Disclosed are compounds of the class of 2-phenylacetamides that modulate the physiological action of the proprotein convertase subtilisin kexin type 9 (PCSK9), and methods of using these modulators to reduce LDL-cholesterol levels and/or for the treatment and/or prevention of cardiovascular disease (CVD), including treatment of hypercholesterolemia.

6 Claims, 29 Drawing Sheets

Specification includes a Sequence Listing.

(51) Int. Cl.

| | |
|---|---|
| C07D 403/12 | (2006.01) |
| C07D 213/74 | (2006.01) |
| C07D 213/82 | (2006.01) |
| C07D 231/12 | (2006.01) |
| C07D 233/90 | (2006.01) |
| C07D 401/06 | (2006.01) |
| C07D 241/04 | (2006.01) |
| C07D 241/08 | (2006.01) |
| C07D 471/04 | (2006.01) |
| C07D 261/08 | (2006.01) |
| C07D 295/14 | (2006.01) |
| C07D 211/70 | (2006.01) |
| A61K 31/167 | (2006.01) |
| A61K 31/17 | (2006.01) |
| A61K 31/18 | (2006.01) |
| A61K 31/235 | (2006.01) |
| A61K 31/397 | (2006.01) |
| A61K 31/401 | (2006.01) |
| A61K 31/415 | (2006.01) |
| A61K 31/4164 | (2006.01) |
| A61K 31/42 | (2006.01) |
| A61K 31/435 | (2006.01) |
| A61K 31/437 | (2006.01) |
| A61K 31/4418 | (2006.01) |
| A61K 31/495 | (2006.01) |
| A61K 31/496 | (2006.01) |
| A61K 31/505 | (2006.01) |
| A61K 31/506 | (2006.01) |
| A61K 31/245 | (2006.01) |
| A61K 31/40 | (2006.01) |
| C07C 275/40 | (2006.01) |
| C07D 211/14 | (2006.01) |
| C07D 211/96 | (2006.01) |
| C07D 213/68 | (2006.01) |

(56) References Cited

U.S. PATENT DOCUMENTS

| | | | |
|---|---|---|---|
| 8,003,654 | B2 | 8/2011 | Aissaoui |
| 2004/0038858 | A1 | 2/2004 | Dorsch et al. |
| 2005/0137230 | A1 | 6/2005 | Dorsch et al. |
| 2008/0090829 | A1 | 4/2008 | Hamanaka |
| 2009/0275053 | A1 | 11/2009 | Horton et al. |
| 2010/0184730 | A1 | 7/2010 | Vu et al. |
| 2010/0233177 | A1 | 9/2010 | Yowe et al. |
| 2011/0009628 | A1 | 1/2011 | Liu et al. |
| 2012/0252796 | A1 | 10/2012 | Pingali et al. |
| 2014/0093513 | A1 | 4/2014 | Milne et al. |
| 2014/0099333 | A1 | 4/2014 | Schwink et al. |

OTHER PUBLICATIONS

PubChem CID 3977521 or MLS000418020, https://pubchem.ncbi.nlm.nih.gov/compound/3977521, entered on Sep. 12, 2005, last accessed on May 3, 2017.*
https://pubchem.ncbi.nlm.nih.gov/compound/2368923, last accessed Aug. 25, 2017. First deposited Sep. 17, 2005.*
https://pubchem.ncbi.nlm.nih.gov/compound/4803336, last accessed Aug. 25, 2017. First deposited Sep. 17, 2005.*
Abifadel, Marianne et al., "Mutations in PCSK9 cause autosomal dominant hypercholesterolemia", Nature Genetics, 34(2): 154-156 (2003).
Benjannet, Suzanne et al., "The Proprotein Convertase (PC) PCSK9 Is Inactivated by Furin and/or PC5/6A", Journal of Biological Chemistry, 281(41): 30561-30572 (2006).
Benjannet, Suzanne et al., "NARC-1/PCSK9 and Its Natural Mutants", The Journal of Biological Chemistry, 279 (47): 48865-48875 (2004).
Bottomley, Matthew J. et al., "Structural and Biochemical Characterization of the Wild Type PCSK9-EGF (AB) Complex and Natural Familial Hypercholesterolemia Mutants", Journal of Biological Chemistry, 284(2): 1313-1323 (2009).
Cohen, Jonathan et al., "Low LDL cholesterol in individuals of African descent resulting from frequent nonsense mutations in PCSK9", Nature Genetics, 37(2): 161-165 (2005).
Crunkhorn, Sarah, "PCSK9 antibody reduces LDL cholesterol", Nature Reviews/Drug Discovery, 11: 11 (2012).
Cunningham, David et al., "Structural and biophysical studies of PCSK9 and its mutants linked to familial hypercholesterolemia", Nature Structural & Molecular Biology, 14(5): 413-419 (2007).
Frank-Kamenetsky, Maria et al., "Therapeutic RNAi targeting PCSK9 acutely lowers plasma cholesterol in rodents and LDL cholesterol in nonhuman primates", PNAS, 105(33): 11915-11920 (2008).
Graham, Mark J. et al., "Antisense inhibition of proprotein convertase subtilisin/kexin type 9 reduces serum LDL in hyperlipidemic mice", Journal of Lipid Research, 48: 763-767 (2007).
Grundy, Scott M. et al., "Implications of Recent Clinical Trials for the National Cholesterol Education Program Adult Treatment Panel III Guidelines", Circulation, 110: 227-239 (2004).
Kwon, Hyock Joo et al., "Molecular basis for LDL receptor recognition by PCSK9", PNAS, 105(6): 1820-1825 (2008).
Li, Jun et al., "Secreted PCSK9 promotes LDL receptor degradation independently of proteolytic activity", Biochem. J., 106: 203-207 (2007).
Maxwell, Kara N. et al., "Adenoviral-mediated expression of PCSK9 in mice results in a low-density lipoprotein receptor knockout phenotype", PNAS, 101(18): 7100-7105 (2004).
McNutt, Markey et al., "Antagonism of Secreted PCSK9 Increases Low Density Lipoprotein Receptor Expression in HepG2 Cells", The Journal of Biological Chemistry, 284(16): 10561-10570 (2009).
McNutt, Markey et al., "Catalytic Activity if Not Required for Secreted PCSK9 to Reduce Low Density Lipoprotein Receptors in HepG2 Cells", Journal of Biological Chemistry, 282(29): 20799-20803 (2007).
Piper, Derek E. et al., "The Crystal Structure of PCSK9: A Regulator of Plasma LDL—Cholesterol", Structure, 15: 545-552 (2007).
Rashid, Shirya et al., "Decreased plasma cholesterol and hypersensitivity to statins in mice lacking PCSK9", PNASA, 102(15): 5374-5379 (2005).
Seidah, Nabil G. et al., "The secretory proprotein convertase neural apoptosis-regulated convertase 1 (NARC-1): Liver recognition and neuronal differentiation", PNAS, 100(3): 928-933 (2003).
Swergold, Gary et al., Core 2. Epidemiology and Prevention of CV Disease: Physiology, Pharmacology and Lifestyle, Circulation, 122: A23251 (2010).
Zhang, Da Wei et al., "Binding of Proprotein Convertase Subtilisin/Kexin Type 9 to Epidermal Growth Factor-like Repeat A of Low Density Lipoprotein Receptor Decreases Receptor Recycling and Increases Degradation", Journal of Biological Chemistry, 282(25): 18602-18612 (2007).
Zhao, Zhenze et al., "Molecular Characterization of Loss-of-Function Mutations in PCSK9 and Identification of a Compound heterozygote", The American Journal of Human Genetics, 79: 514-523 (2006).
Amgen, "Ascending Multiple Dose Study to Evaluate the Safety, Tolerability, Pharmacokinetics and Pharmacodynamics of Evolocumab (AMG 145) in Adults with Hyperlipidemia on Stable Doses of a Statin", CinicalTrials.gov (2010).
International Search Report/Written Opinion, dated Aug. 29, 2014, issued in corresponding International Application No. PCT/US2014/022957, filed Mar. 11, 2014.
Pisciotta, Livia et al., "Additive effect of mutations in LDLR and PCSK9 genes on the phenotype of familial hypercholesterolemia", Atherosclerosis, 186: 433-440 (2006).
International Search Report/Written Opinion, dated Aug. 13, 2014, issued in corresponding International Application No. PCT/US2014/023135, filed Mar. 11, 2014.
Yangthara, Buranee et al., "Small-Molecule Vasopressin-2 Receptor Antagonist Identified by a G-Protein Coupled Receptor Pathway Screen", Molecular Pharmacology, 72(1): 86-94 (2007).

(56) References Cited

OTHER PUBLICATIONS

Extended European Search Report, dated Aug. 8, 2016, issued in related European Application No. 14770138.7, filed Mar. 11, 2014.
Ghosh, Partha et al., "Resolution of Carboxylic Acids Using Copper(I)-Promoted Removal of Propargylic Esters under Neutral Conditions", J. Org. Chem., 76: 4168-4172 (2011).
First Office Action, dated Mar. 13, 2017, issued in corresponding Chinese Patent Application No. 201480016207.6 (in English and Chinese).

* cited by examiner

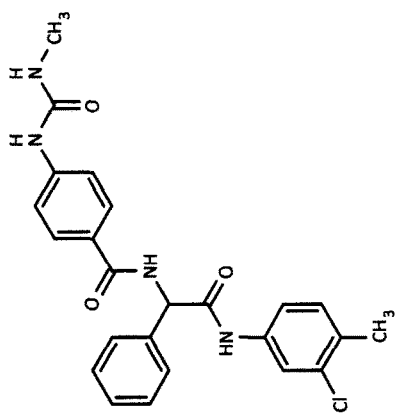
SBC-110,741
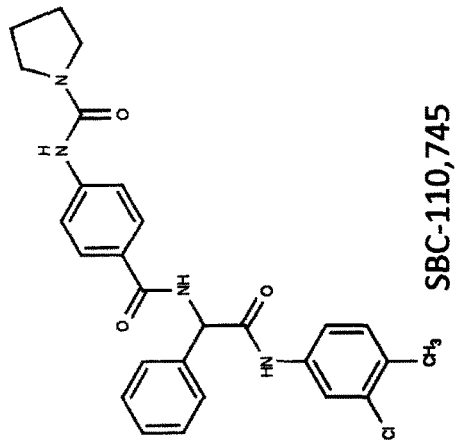
SBC-110,745
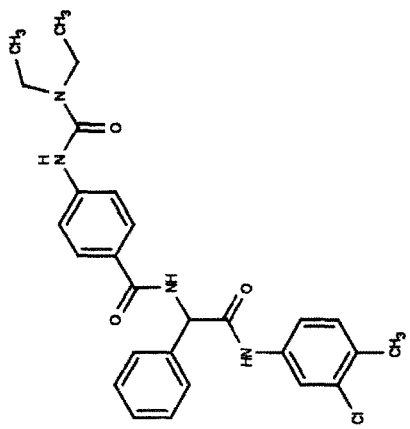
SBC-110,740
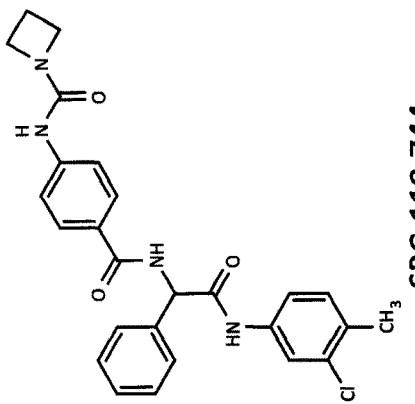
SBC-110,744
FIGURE 1 (CONTINUED)

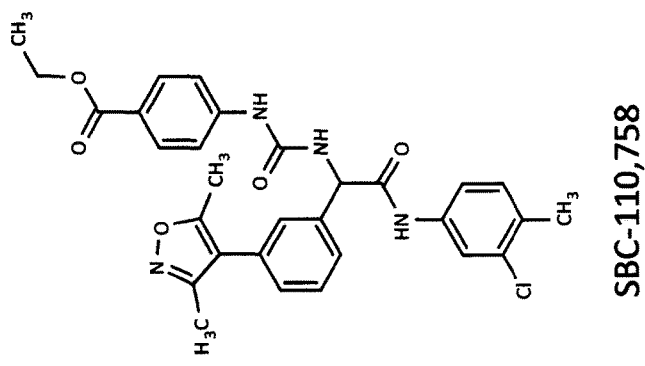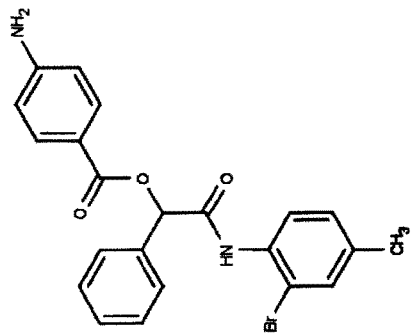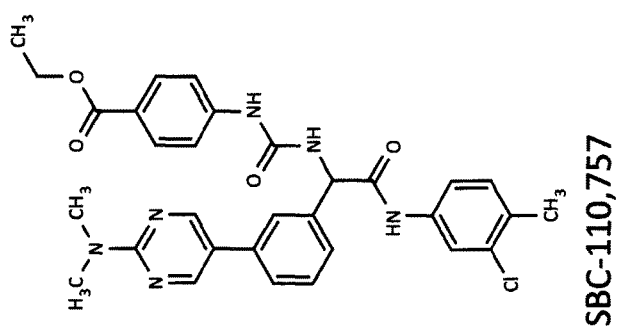
FIGURE 1 (CONTINUED)

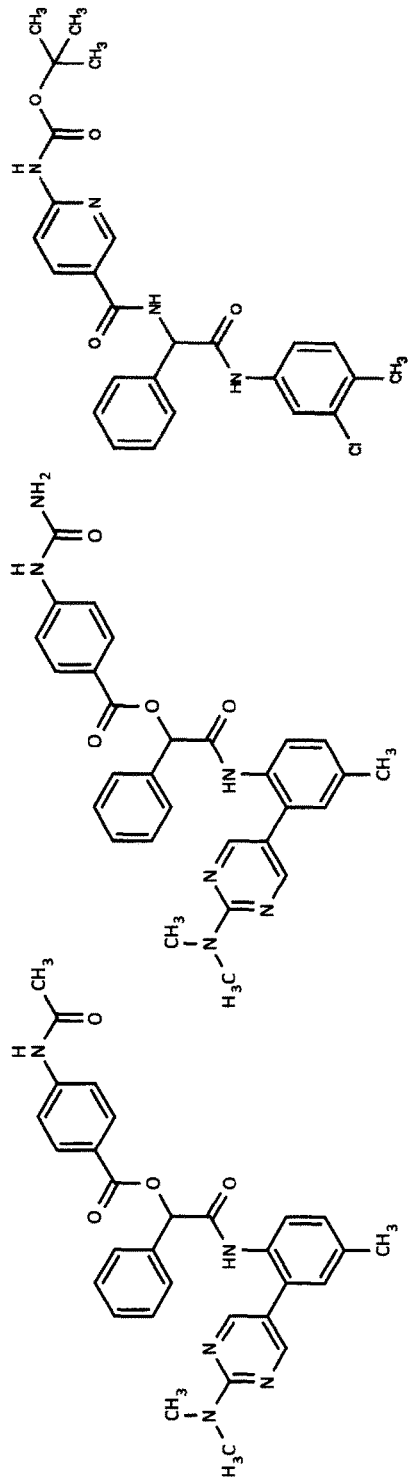
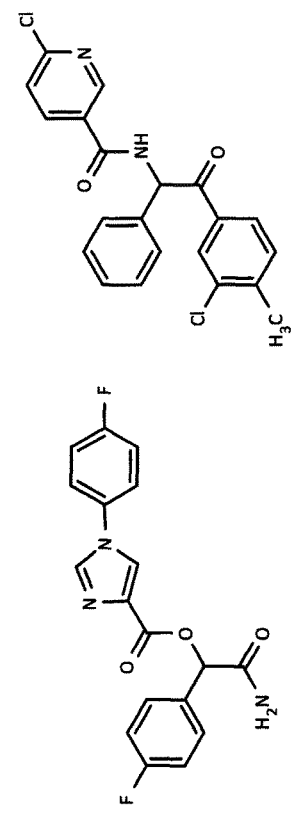
FIGURE 1 (CONTINUED)

```
         10         20         30         40         50         60
MGTVSSRRSW WPLPLLLLLL LLLGPAGARA QEDEDGDYEE LVLALRSEED GLAEAPEHGT 70         80         90        100        110        120
TATFHRCAKD PWRLPGTYVV VLKEETHLSQ SERTARRLQA QAARRGYLTK ILHVFHGLLP 130        140        150        160        170        180
GFLVKMSGDL LELALKLPHV DYIEEDSSVF AQSIPWNLER ITPPRYRADE YQPPDGGSLV 190        200        210        220        230        240
EVYLLDTSIQ SDHREIEGRV MVTDFENVPE EDGTRFHRQA SKCDSHGTHL AGVVSGRDAG 250        260        270        280        290        300
VAKGASMRSL RVLNCQGKGT VSGTLIGLEF IRKSQLVQPV GPLVVLLPLA GGYSRVLNAA 310        320        330        340        350        360
CQRLARAGVV LVTAAGNFRD DACLYSPASA PEVITVGATN AQDQPVTLGT LGTNFGRCVD 370        380        390        400        410        420
LFAPGEDIIG ASSDCSTCFV SQSGTSQAAA HVAGIAAMML SAEPELTLAE LRQRLIHFSA 430        440        450        460        470        480
KDVINEAWFP EDQRVLTPNL VAALPPSTHG AGWQLFCRTV WSAHSGPTRM ATAVARCAPD 490        500        510        520        530        540
EELLSCSSFS RSGKRRGERM EAQGGKLVCR AHNAFGGEGV YAIARCCLLP QANCSVHTAP 550        560        570        580        590        600
PAEASMGTRV HCHQQGHVLT GCSSHWEVED LGTHKPPVLR PRGQPNQCVG HREASIHASC 610        620        630        640        650        660
CHAPGLECKV KEHGIPAPQE QVTVACEEGW TLTGCSALPG TSHVLGAYAV DNTCVVRSRD 670        680        690
VSTTGSTSEG AVTAVAICCR SRHLAQASQE LQ
```

SEQ ID NO: 1

FIGURE 2

| Group | Treatment Groups |
|---|---|
| Normal diet - 6 mice | No treatment |
| High fat diet - 7 mice | No treatment |
| High fat diet - 7 mice | SBC-110,686 |
| High fat diet - 5 mice | SBC-110,733 |
| High fat diet - 4 mice | SBC-110,736 |

FIGURE 14

ANTI-PCSK9 COMPOUNDS AND METHODS FOR THE TREATMENT AND/OR PREVENTION OF CARDIOVASCULAR DISEASES

CROSS-REFERENCE TO RELATED APPLICATIONS

This application is a 371 of International Application No. PCT/US2014/023135, filed Mar. 11, 2014, which claims the benefit of U.S. Provisional Application No. 61/789,867, filed Mar. 15, 2013, the entire disclosure of each of the aforesaid applications is incorporated by reference in the present specification.

STATEMENT REGARDING FEDERAL SPONSORED RESEARCH OR DEVELOPMENT

The present invention was made with support from the National Heart, Lung and Blood Institute (NHLBI) under SBIR Grant No. HL092712. The U.S. Government has certain rights in this invention.

FIELD OF INVENTION

The present invention relates to compounds that modulate the physiological action of the proprotein convertase subtilisin kexin type 9 (PCSK9), including its interaction with the low density lipoprotein receptor (LDLR). More specifically, the invention relates to compositions comprising small molecule modulators of PCSK9 function and methods of using these modulators as a medicament. The small molecule modulators of PCSK9 function can be used therapeutically to lower LDL-cholesterol levels in blood, and can be used in the prevention and/or treatment of cholesterol and lipoprotein metabolism disorders, including familial hypercholesterolemia, atherogenic dyslipidemia, atherosclerosis, and, more generally, cardiovascular disease (CVD).

BACKGROUND OF INVENTION

Cardiovascular diseases are the leading cause of death, with atherosclerosis being the leading cause of cardiovascular diseases. Atherosclerosis is a disease of the arteries and is responsible for coronary heart disease associated with many deaths in industrialized countries. Several risk factors for coronary heart disease have now been identified: dyslipidemia, hypertension, diabetes, smoking, poor diet, inactivity and stress. Dyslipidemia is elevation of plasma cholesterol (hypercholesterolemia) and/or triglycerides (TGs) or a low high-density lipoprotein (HDL) level that contributes to the development of atherosclerosis. It is a metabolic disorder that is proven to contribute to cardiovascular disease. In the blood, cholesterol is transported in lipoprotein particles, where the low-density lipoprotein (LDL) cholesterol (LDL-C) is considered "bad" cholesterol, while HDL-cholesterol (HDL-C) is known as "good" cholesterol. Lipid and lipoprotein abnormalities are extremely common in the general population and are regarded as a highly modifiable risk factor for cardiovascular disease, due to the influence of cholesterol on atherosclerosis. There is a long-felt significant unmet need with respect to CVD with 60-70% of cardiovascular events, heart attacks and strokes occurring despite the treatment with statins (the current standard of care in atherosclerosis). Moreover, new guidelines suggest that even lower LDL levels should be achieved in order to protect high risk patients from premature CVD (1).

The establishment of a link between PCSK9 and cholesterol metabolism was rapidly followed by the discovery that selected mutations in the PCSK9 gene caused autosomal dominant hypercholesterolemia (2), suggesting that the mutations confer a gain-of-function (3) by increasing the normal activity of PCSK9. This was supported by the experiment in which wild-type and mutant PCSK9 (S127R and F216L) were expressed at high levels in the livers of mice; hepatic LDLR protein levels fell dramatically in mice receiving either the wild-type or mutant PCSK9 (4, 5). No associated reductions in LDLR mRNA levels were observed, indicating that overexpression of PCSK9, whether mutant or wild-type, reduces LDLRs through a post-transcriptional mechanism.

Given that gain-of-function mutations in PCSK9 cause hypercholesterolemia, it was reasonable to ask if loss-of-function mutations would have the opposite effect and result in hypocholesterolemia. Three loss-of-function mutations in PCSK9 (Y142X, L253F, and C679X) were identified in African-Americans (6). These mutations reduce LDL-C levels by 28% and were shown to decrease the frequency of CHD (defined as myocardial infarction, coronary death or coronary revascularization) by 88%. Rashid et al. (7) studied the mechanism of loss-of-function mutations in mice where PCSK9 was inactivated. They reported that these knockout mice showed increased hepatic LDLR protein (but not mRNA), increased clearance of circulating lipoproteins and reduced plasma cholesterol levels. Structure-function relationship analysis of the naturally occurring mutations in PCSK9 has also provided insights into the mechanism of action of PCSK9. Interestingly, mutations in PCSK9 that were found to be associated with the greatest reductions in LDL-C plasma levels are those that prevent the secretion of mature PCSK9 by disrupting its synthesis (Y142X), autocatalytic processing (L253F), or folding (C679X) (8). The Y142X mutation produces no detectable protein because it occurs early in the transcript and is predicted to initiate nonsense-mediated mRNA decay. Mutations in the catalytic domain (L253F) interfere with the autocatalytic cleavage of the protein. In cells expressing the PCSK9-253F, the amount of mature protein was reduced compared to that in cells expressing PCSK9-WT, suggesting that the mutation inhibits autocatalytic cleavage. The L253F mutation is near the catalytic triad (PCSK9 is a serine protease), therefore it might disrupt the active site (8). Inasmuch as autocatalytic cleavage of PCSK9 is required for export of the protein out of the ER, the L253F mutation delays transport of PCSK9 from the ER to the cell surface. The nonsense mutation (C679X) in PCSK9, which truncates the protein by 14 amino acids, did not interfere with protein processing, but the mature protein accumulates in the cells and none is secreted, suggesting that the protein is cleaved normally but is misfolded and is retained in the ER (8, 9).

The mechanism by which PCSK9 causes the degradation of the LDLR has not been fully elucidated. However, it is clear that the protease activity of PCSK9 is not required for LDLR degradation (10, 11). Li et al. (10) have co-expressed the prodomain and the catalytic domain in trans, and showed that the secreted PCSK9 was catalytically inactive, yet it is functionally equivalent to the wild-type protein in lowering cellular LDL uptake and LDLR levels. Similar studies were also reported by McNutt et al. (11). Furthermore, Zhang et al. (12) has mapped PCSK9 binding to the EGF-A repeat of the LDLR, and showed that such binding decreases the receptor recycling and increases its degradation. They also reported that binding to EGF-A domain was calcium-dependent and increased dramatically with reduction in pH from 7 to 5.2. Recently, Kwon et al. (13) determined the crystal structure of PCSK9 in complex with the LDLR-EGF-AB (EGF-A and EGF-B). The structure shows a well defined EGF-A domain, but the EGF-B domain is disordered and absent from their electron density map. The EGF-A domain binds to the PCSK9 catalytic domain at a site distant from the catalytic site, and makes no contact with either the C-terminal domain or the prodomain (14).

Several strategies have been proposed for targeting PCSK9 (15). Strategy 1: mRNA knockdown approaches include the use of antisense oligonucleotides or RNAi. Antisense oligonucleotides administered to mice reduced PCSK9 expression by >90% and lowered plasma cholesterol levels by 53% (16). A single intravenous injection of an RNAi delivered in lipidoid nanoparticles to cynomologous monkeys reduced plasma PCSK9 levels by 70% and plasma LDL-C levels by 56% (17). Strategy 2: is to prevent binding of PCSK9 to the LDLR on the cell surface with a small molecule, a peptide, or an antibody directed against PCSK9. Adding EGF-A fragments to cultured cells inhibits the ability of exogenously added PCSK9 to mediate LDLR degradation. Strategy 3: is to develop small-molecule inhibitors of the PCSK9 processing. Despite evidence that the catalytic activity of PCSK9 is not required for LDLR degradation (11), an intracellular inhibitor of PCSK9 catalytic activity should be effective, since autocatalytic processing of PCSK9 is required for secretion of the protein from the ER. Following its synthesis, PCSK9 undergoes an autocatalytic cleavage reaction that clips off the prodomain, but the prodomain remains attached to the catalytic domain (18, 19). The autocatalytic processing step is required for the secretion of PCSK9 (20), likely because the prodomain serves as a chaperone and facilitates folding. The continued attachment of the prodomain partially blocks the substrate binding pocket of PCSK9 (18, 19). McNutt et al. (21) demonstrated that antagonism of secreted PCSK9 increases LDLR expression in HepG2 cells. They show that an FH-associated LDLR allele (H306Y) that results in a gain-of-function mutation is due to an increase in the affinity of PCSK9 to the LDLR, which would lead to enhanced LDLR destruction, and decreased plasma LDL-C clearance. Furthermore, they were able to show elegantly that blocking the secreted PCSK9 with LDLR (H306Y) subfragment resulted in an increase in the level of LDLR in cultured HepG2 cells. Therefore, PCSK9 acts as a secreted factor to cause LDLR degradation, and a small molecule inhibitor that interferes with the autocatalytic process should decrease the amount of mature secreted PCSK9. This invention relates to identification of small molecules that down-regulate the function of PCSK9 using Strategy 3.

Recently (22-24), Regeneron/Sanofi and Amgen have reported Phase II proof-of-concept data that validate the blocking of PCSK9 with a monoclonal antibody as a strategy for lowering LDL-C in patients not controlled on standard statin therapy. They reported that a single injection of their drug, called REGN727, slashed LDL levels by more than 60% in clinical trial. Their approach follows Strategy 2 using antibodies instead of small molecules. This Strategy 2 is also being pursued by Merck, Novartis and Pfizer, while Strategy 1 is being pursued by Alnylam, Idera and Santaris (25).

SUMMARY OF THE INVENTION

This invention relates to small molecules that selectively interact with and down modulate PCSK9 function. In a first embodiment, the agents used in the practice of this invention have the general formula:

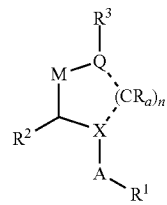

(I)

wherein $R^1$, $R^2$ and $R^3$ are independently selected from the group consisting of H and optionally substituted lower alkyl, alkenyl, cycloalkyl, aryl, heterocycle, and heteroaryl;

X is O and $NR^4$; $R^4$ is selected from the group consisting of H and lower alkyl;

A is CO, $CONR^5$, $SO_2$, C(=O)—O or a valence bond to $R^1$; $R^5$ is selected from the group consisting of H and lower alkyl;

M is CO and $CR^6R^7$; $R^6$ and $R^7$ are independently selected from the group consisting of H, lower alkyl;

Q is selected from the group consisting of O, and $NR^8$; $R^8$ is selected from the group consisting of H, lower alkyl, or optionally when X is $NR^4$ and Q is $NR^8$, $R^4$ and $R^8$ and the nitrogen atom to which each of $R^4$ and $R^8$ is attached complete an optionally substituted 5- or 6-membered heterocycle ring, as represented by —$(CR_a)_n$—, wherein $R_a$ represents H or lower alkyl and n=1 or 2; and the pharmaceutically acceptable salts and all stereoisomers of the compound. The compounds of formula I are believed to be novel compounds, with the exception of [(3-chloro-4-methylphenyl)carbamoyl](phenyl)methyl 4-(carbamoylamino)benzoate.

In one embodiment, the present invention provides a method for the treatment or prophylaxis of hypercholesterolemia, and/or at least one symptom of dyslipidemia, atherosclerosis, CVD or coronary heart disease in a patient in need of such treatment comprising administering to such patient a therapeutically effective amount of a compound of formula I, above.

In another embodiment, the present method for the treatment or prophylaxis of hypercholesterolemia, and/or at least one symptom of dyslipidemia, atherosclerosis, CVD or coronary heart disease in a patient in need of such treatment, is practiced by administering to a patient in need of such treatment or prophylaxis at least one of the following compounds:

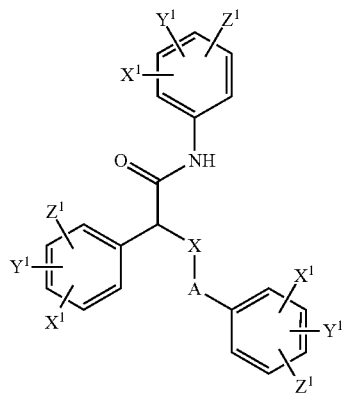

(II)

wherein $X^1$, $Y^1$ and $Z^1$ are the same or different and each represents hydrogen or a substituent from the group consisting of hydroxyl, halogen, amino, alkoxy, carboxy, amido (including formamido, alkylamido and arylamido), aminocarbonylamino, monoalkylaminocarbonylamino, dialkylaminocarbonylamino, carbamato, carboxamido, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinyl and, optionally substituted, lower alkyl, alkenyl, alkynyl, cycloalkyl, aryl, heterocycle, and heteroaryl;

X is O and $NR^4$; $R^4$ is selected from the group consisting of H and lower alkyl;

A is CO, $CONR^5$, and $SO_2$; $R^5$ is selected from the group consisting of H and lower alkyl.

In alternative embodiments of the above-described method, a patient in need of such treatment or prophylaxis is administered at least one of the following compounds:

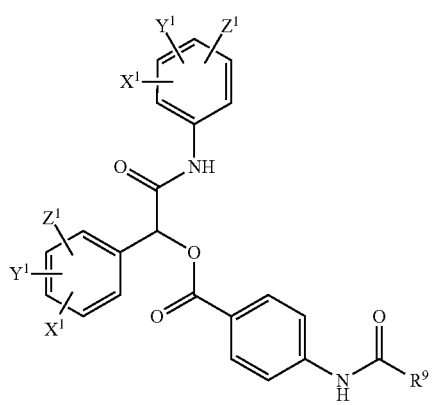

(III)

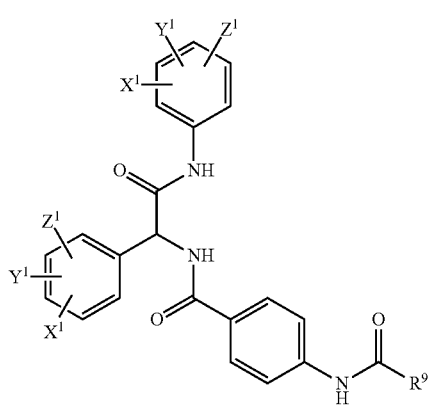

(IV)

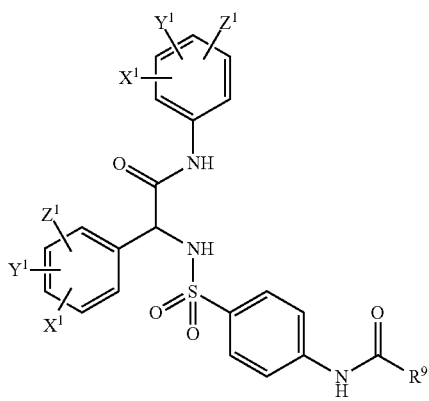

(V)

wherein, in each of Formulas III, IV and V, $X^1$, $Y^1$ and $Z^1$ are the same or different and each represents hydrogen or a substituent selected from the group consisting of hydroxy, halogen, amino, alkoxy, carboxy, aminocarbonylamino, monoalkylaminocarbonylamino, dialkylaminocarbonylamino, carbamato, amido (including formamido, alkylamido and arylamido), aminocarbonylamino, monoalkylaminocarbonylamino, dialkylamino, carboxylamino, carbamato, carboxamido, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinyl and, optionally substituted, lower alkyl, alkenyl, alkynyl, cycloalkyl, aryl, heterocycle, and heteroaryl; $R^9$ is selected from the groups consisting of H, $OR^{10}$, and $NR^{10}R^{11}$; $R^{10}$ and $R^{11}$ are independently selected from the group consisting of H and optionally substituted lower alkyl, alkenyl, aryl, heteroaryl, or heterocycle, or taken together form an optionally substituted heterocycle.

In another embodiment, the method of the invention involves the administration of at least one compound of the formula:

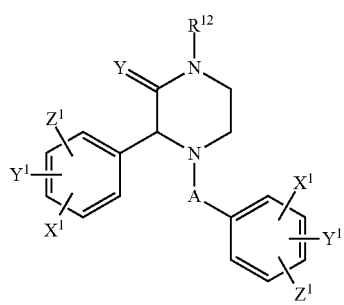

(VI)

wherein $X^1$, $Y^1$ and $Z^1$ are the same or different and each represents hydrogen or a substituent selected from the group consisting of hydroxy, halogen, amino, alkoxy, carboxy, aminocarbonylamino, monoalkylaminocarbonylamino, dialkylaminocarbonylamino, carbamato, amido (including formamido, alkylamido and arylamido), carboxamido, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinyl and, optionally substituted, lower alkyl, alkenyl, alkynyl, cycloalkyl, aryl, heterocycle, and heteroaryl; $R^{12}$ is selected from the group consisting of H and optionally substituted lower alkyl, alkenyl, alkynyl, cycloalkyl, aryl, heterocycle, and heteroaryl;

A is CO and $SO_2$;

Y is $H_2$ or O.

In the last-mentioned embodiment, the compound administered may be at least one of the formula:

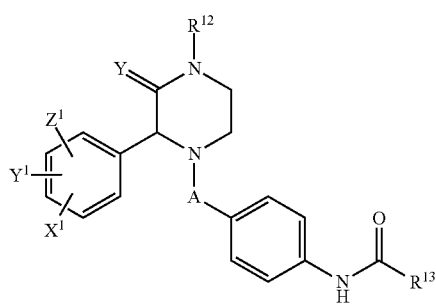

(VII)

wherein $X^1$, $Y^1$ and $Z^1$ are the same or different and each represents hydrogen or a substituent selected from the group consisting of hydroxy, halogen, amino, alkoxy, carboxy, amido (including formamido, alkylamido and arylamido), carboxamido, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinyl and, optionally substituted, lower alkyl, alkenyl, alkynyl, cycloalkyl, aryl, heterocycle, and heteroaryl; $R^{12}$ is selected from the group consisting of H and optionally substituted lower alkyl, alkenyl, alkynyl, cycloalkyl, aryl, heterocycle, and heteroaryl; $R^{13}$ is selected from the groups consisting of H, $OR^{14}$, and $NR^{14}R^{15}$; $R^{14}$ and $R^{15}$ are independently selected from the group consisting of H and optionally substituted lower alkyl, alkenyl, aryl, heteroaryl, or heterocycle, or taken together when attached to a nitrogen atom form an optionally substituted heterocycle;

A is CO and $SO_2$;

Y is $H_2$ or O.

In another embodiment of the invention, the compound administered may be a compound of formula VIII:

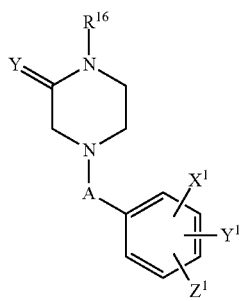

(VIII)

wherein $X^1$, $Y^1$ and $Z^1$ are the same or different and each represents hydrogen or a substituent selected from the group consisting of hydroxy, halogen, amino, alkoxy, carboxy, amido (including formamido, alkylamido and arylamido), carboxamido, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinyl and, optionally substituted, lower alkyl, alkenyl, alkynyl, cycloalkyl, aryl, heterocycle, and heteroaryl; $R^{16}$ is selected from the group consisting of H and optionally substituted lower alkyl, alkenyl, alkynyl, cycloalkyl, aryl, heterocycle, and heteroaryl; A is CO and $SO_2$; and Y is $H_2$ or O. In a preferred embodiment of formula VIII, at least one of $X^1$, $Y^1$ and $Z^1$ is 4-$NHCOR^{17}$; wherein $R^{17}$ is selected from the groups consisting of H, $OR^{18}$, and $NR^{18}R^{19}$; $R^{18}$ and $R^{19}$ are independently selected from the group consisting of H and optionally substituted lower alkyl, alkenyl, aryl, heteroaryl, or heterocycle, or taken together when attached to a nitrogen atom form an optionally substituted heterocycle.

In another aspect, the agents used in the practice of this invention may have the general formula:

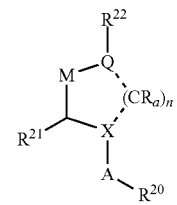

(IX)

wherein $R^{20}$, $R^{21}$ and $R^{22}$ are independently selected from the group consisting of H and optionally substituted lower alkoxy, alkylamino, alkyl, alkenyl, cycloalkyl, aryl, heterocycle, and heteroaryl;

X is O and $NR^{23}$; $R^{23}$ is selected from the group consisting of H and lower alkyl, or optionally taken together with Q or $R^1$ and the atoms to which each is attached forms an optionally substituted 5- or 6-membered ring;

A is CO, $CONR^{24}$, $SO_2$, C(=O)—O or a valence bond to $R^{20}$; $R^{24}$ is selected from the group consisting of H and lower alkyl;

M is CO and $CR^{25}R^{26}$; $R^{25}$ and $R^{26}$ are independently selected from the group consisting of H, lower alkyl, a bond to Q, or optionally taken together with $R^{22}$ and the atoms to which each is attached forms an optionally substituted aryl, heteroaryl, or heterocycle ring;

Q is selected from the group consisting of O, $NR^{27}$, or a valence bond to $R^{22}$; $R^{27}$ is selected from the group consisting of H, lower alkyl, or optionally when X is $NR^{23}$ and Q is $NR^{27}$, $R^{23}$ and $R^{27}$ and the nitrogen atom to which each of $R^{23}$ and $R^{27}$ is attached complete an optionally substituted 5- or 6-membered heterocycle ring, as represented by —$(CR_a)_n$—, wherein $R_a$ represents H or lower alkyl and n=1 or 2; and the pharmaceutically acceptable salts and all stereoisomers of the compound.

DESCRIPTION OF DRAWINGS AND TABLES

FIG. 1 sets forth the structures of selected compounds of the invention. Listed compounds show LDLR fold-increase (upregulation) relative to control (no inhibitor) ranging from 1.5 and 30-fold (@25 uM in HEK293 cells).

FIG. 2 sets forth an exemplary amino acid sequence for human PCSK9, found as Uniprot Accession Number Q8NBP7 (SEQ ID NO: 1).

FIG. 3 shows the effect of various concentrations of different compounds on PCSK9 processing in HEK293 transfected cells. HEK-293T cells were seeded into 96 well plates in a DMEM containing 10% Fetal Bovine Serum media and incubated overnight at 37° C. Cells were transfected with PCSK9 cDNA construct. Compounds (1-50 uM) were added, followed by additional 43 hours of incubation. Prior to the PCSK9 assay, the cell media was replaced with serum free media containing the same concentration of compounds or vehicle, and incubated for additional 5 hrs. The cell media was analyzed for PCSK9 secretion and cell viability determined.

FIG. 4 shows the effect of increased degradation of the LDLR by PCSK9. HEK-293T cells were seeded in a DMEM containing 10% Fetal Bovine Serum media and incubated overnight at 37° C. Cells were transfected with Mock (lanes 1 and 2), PCSK9 (lanes 3 and 4), LDRR & PCSK9 (lanes 5 and 6), LDLR (lanes 7 and 8) cDNA constructs. Cells were incubated for additional 48 hrs, and cells and media were analyzed as above.

FIG. 5 shows the upregulation of LDLR by PCSK9 antagonists. HEK-293T cells were seeded in a DMEM containing 10% Fetal Bovine Serum media and incubated overnight at 37° C. Cells were transfected with LDLR & PCSK9 cDNA constructs. After 24 hrs, cells were treated with different concentration compounds and incubated for additional 48 hrs. Cells were lysed and assayed as described above for LDLR expression.

FIG. 6 shows the effect of specific PCSK9 modulators (400 nM concentration) on LDLR upregulation in HepG2 cells. PCSK9 transfected HepG2 cells were seeded into 96 well plates in a MEM containing 10% Fetal Bovine Serum media. Compounds were added, followed by additional 43 hours of incubation. The cells were lysed and analyzed for LDLR expression and cell viability determined as described above.

FIG. 7 shows the increase uptake of Fluorescent Dil-LDL using various concentrations of PCSK9 inhibitor in HepG2 cells. The identified SBC compounds were validated for their ability to increase uptake of Fluorescent Dil-LDL in HepG2 cells. The data show that an increase in the Fluorescent Dil-LDL uptake using low μM concentrations of SBC compounds.

FIG. 8 illustrates a general synthesis route for compounds of the Formula III, wherein the diversity elements are introduced in the last step. The phenyl urea terminus is initially generated by reacting available methyl 4-isocyanatobenzoate with ammonia, then after saponification the benzoic acid intermediate is converted to an acid chloride then coupled with commercial ethyl mandelate. After a second saponification, a library of compounds of the Formula III can be generated through coupling a set of anilines under standard conditions.

FIG. 9 illustrates a general synthesis route for compounds of the Formulas IV and V, above. The versatile phenyl glycine intermediate(s), 3 derived from coupling various anilines to Boc-phenyl glycine, can be benzoylated with commercial or readily synthesized aryl acid chlorides to provide, after any subsequent elaboration, compounds exemplified by SBC-110,716. Similarly, aryl sulfonylation of intermediate(s), 3 provide, after any subsequent elaboration, compounds exemplified by SBC-110,717 and SBC-110,728. Compounds of Formula V can be made using the same synthetic route as that for compounds of Formula IV, but replacing 4-ureido-benzene acid chloride with commercial 4-ureido-benzenesulfonyl chloride.

FIG. 10 illustrates a general synthesis route for compounds of the Formula VI (A is CO, $SO_2$; Y is O). The synthesis begins with commercial 3-phenyl-piperazin-2-one. After Boc protection, the first diversity element, $R_{12}$ is introduced through an N-arylation cross-coupling reaction with an aryl bromide. After Boc removal, the second diversity element can be introduced through reaction of available or synthesized benzoyl chloride or aryl-sulfonyl chloride derivatives to provide compounds of the Formula VII (e.g., SBC-110,761, FIG. 1).

FIG. 11 illustrates a general synthesis route for compounds of the Formula VII (A is CO, $SO_2$). The syntheses begin with commercial 2-phenyl-piperazine. After selective N-arylation with a substituted phenyl bromide under cross-coupling conditions to provide intermediate 14, reaction with either 4-nitrobenzoyl chloride or 4-nitrobenzene sulfonyl chloride and subsequent nitro reduction provides key aniline intermediates, 15 and 16, respectively. Elaboration of the anilines, 15 with sodium cyanate in acetic acid provides mixtures of ureas (SBC-110,733 and SBC-110,734) and acetamides (SBC-110,735, SBC-110,736, and SBC-110,769), while anilines 16 under the same conditions provide the urea (17) and the acetamide (SBC-110,771).

FIG. 12 illustrates a general synthesis route for compounds of the Formula VIII (A is CO) as exemplified by SBC-110,725 and SBC-110,726. The synthesis begins with commercial 2-(piperazin-1-yl)pyrimidine (7). Compounds of the Formula VIII (A is $SO_2$) can also be prepared using the same synthesis route, but replacing a benzoic acid analog with a benzenesulfonyl chloride analog in the reaction with 7.

FIG. 13 illustrates a general synthesis route for additional compounds of the Formula VIII (A is CO). The synthesis begins with commercial Boc-piperazine and its alkylation with a 2-chloromethyl pyridine derivative. After benzoylation with 4-nitrobenzoyl chloride and subsequent nitro reduction, the aniline can be elaborated into a formamide (SBC-110,729) with sodium cyanate and formic acid, or a urea (12) and an acetamide (SBC-110,730) result when sodium cyanate and acetic acid are used.

FIG. 14 shows the different treatments for each of the five groups of animals used to test the efficacy of our compounds.

DETAILED DESCRIPTION OF THE INVENTION

Figure 1:
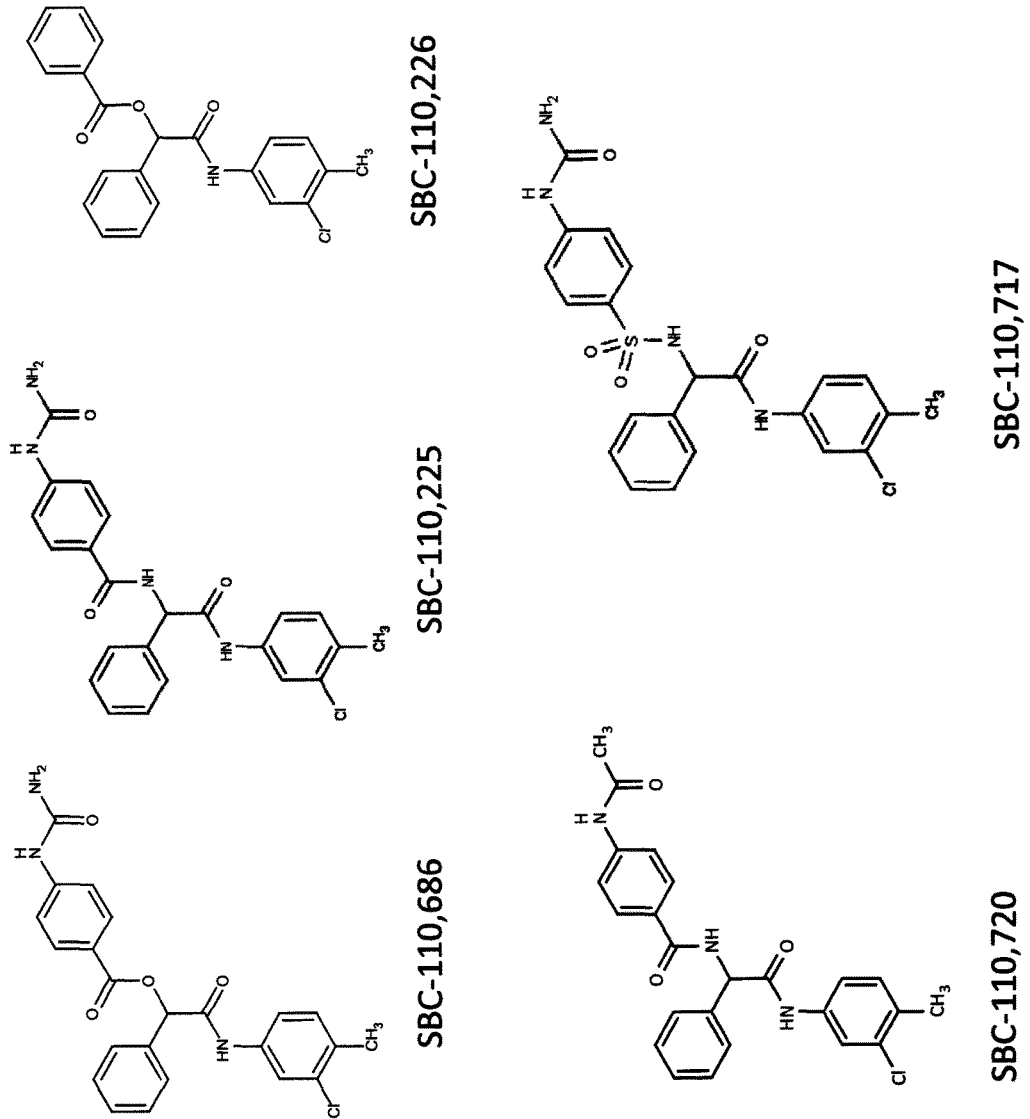
Figure 1:
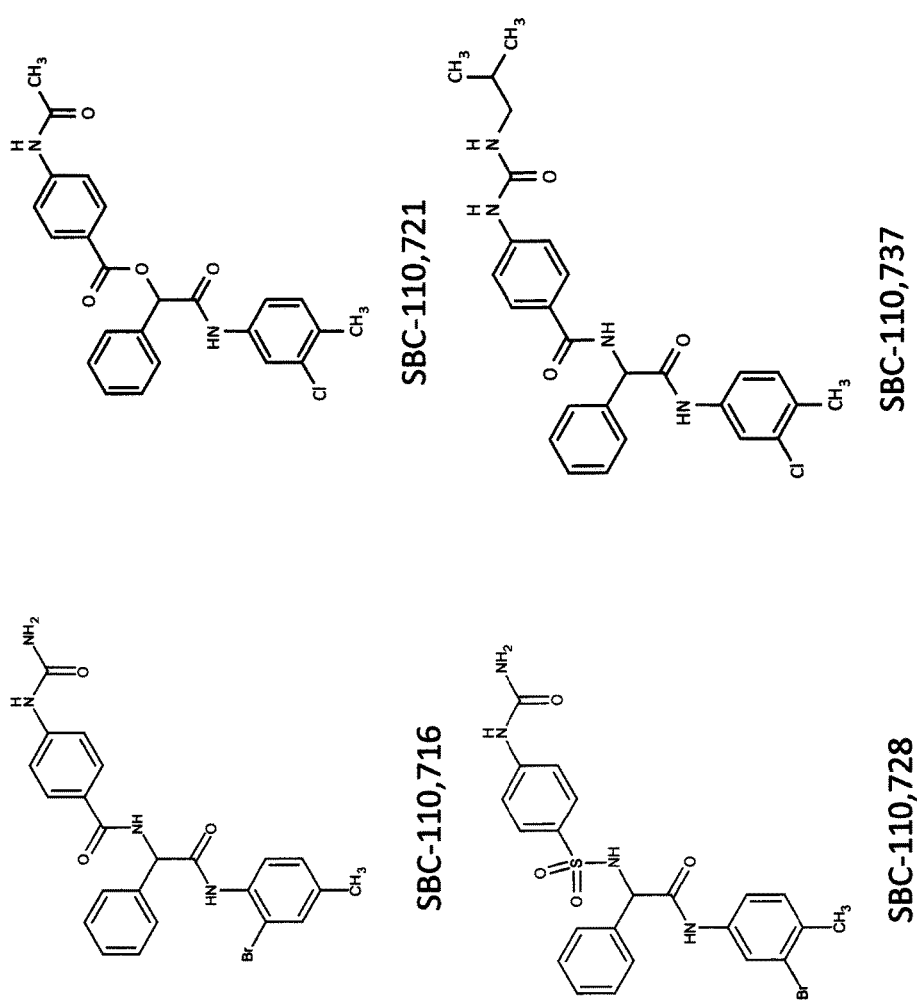
Figure 1:
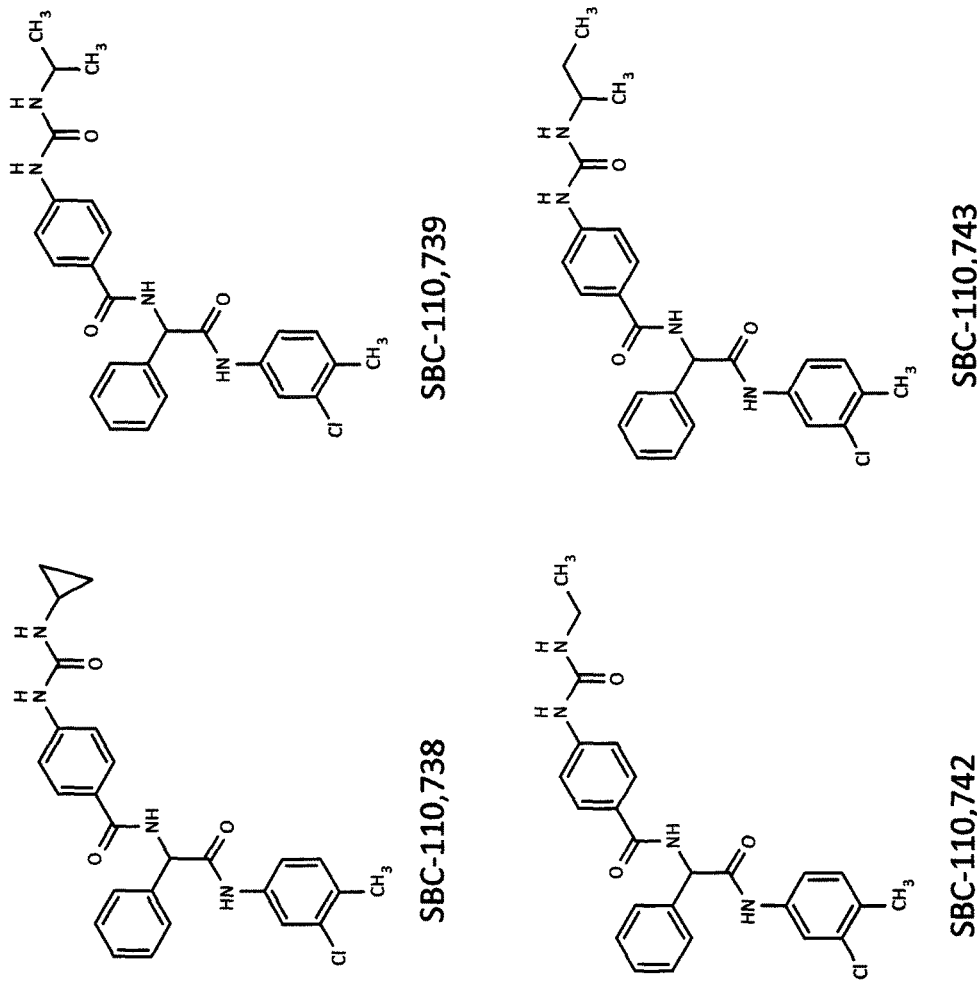
Figure 1:
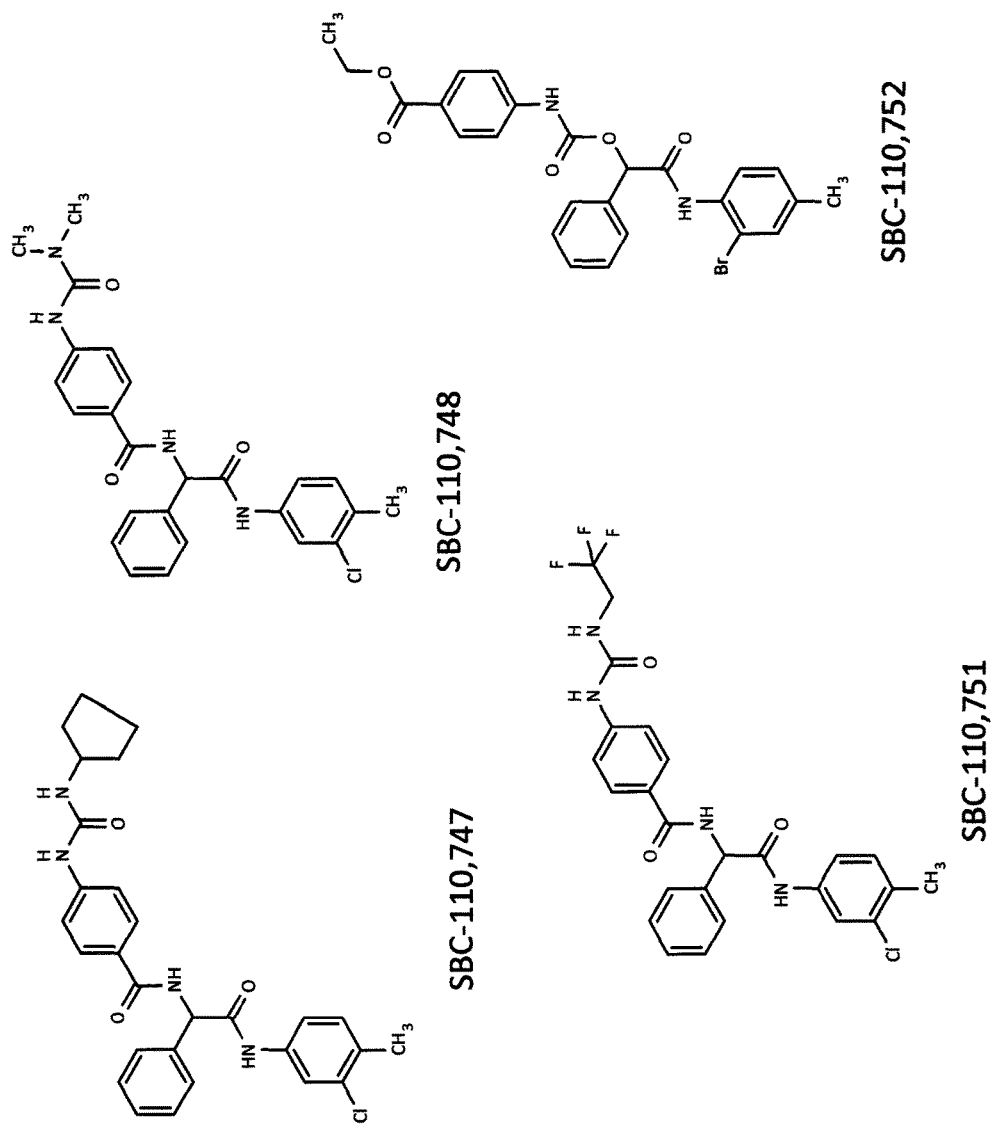
Figure 1:
Figure 1:
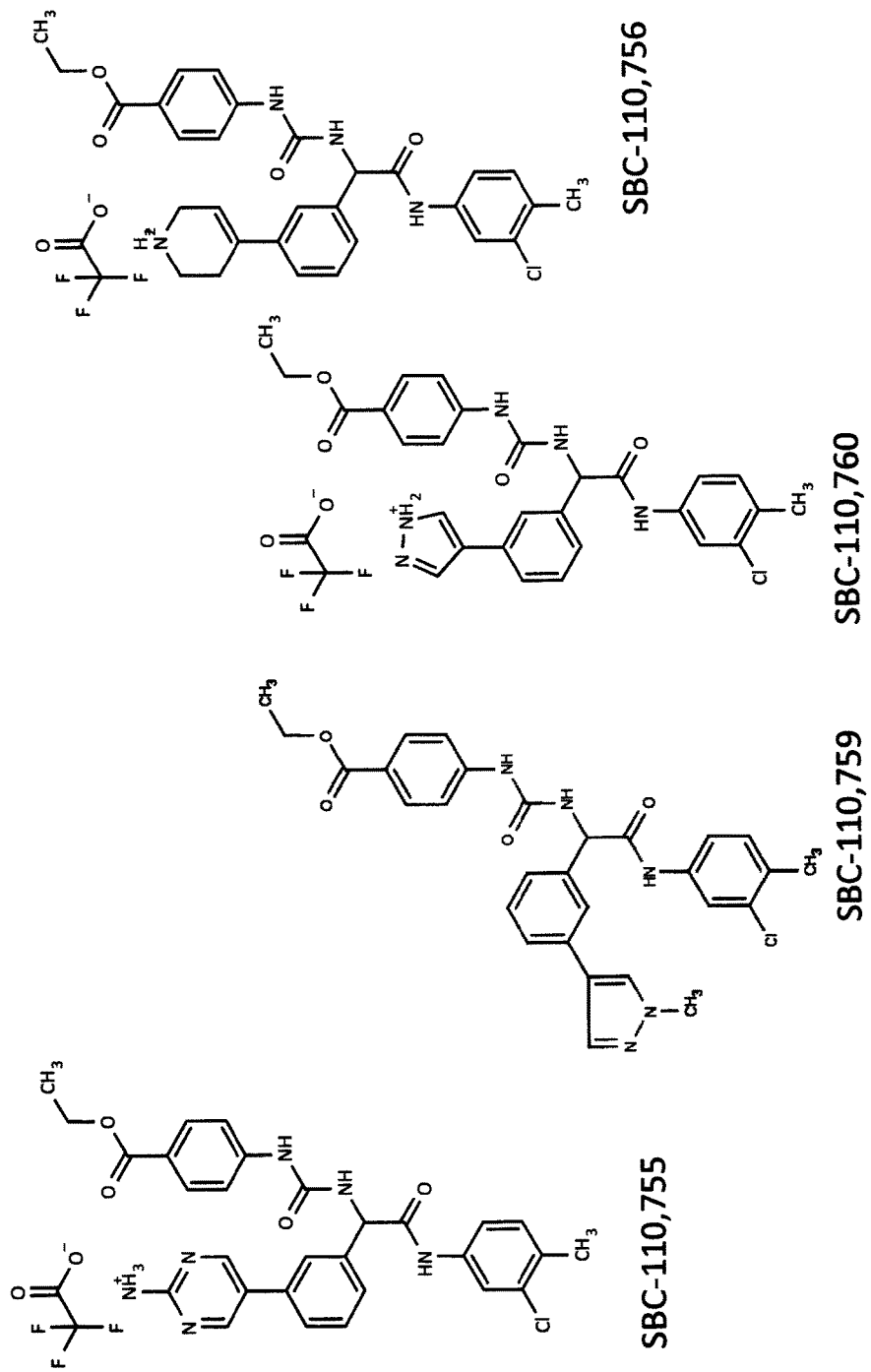
Figure 1:
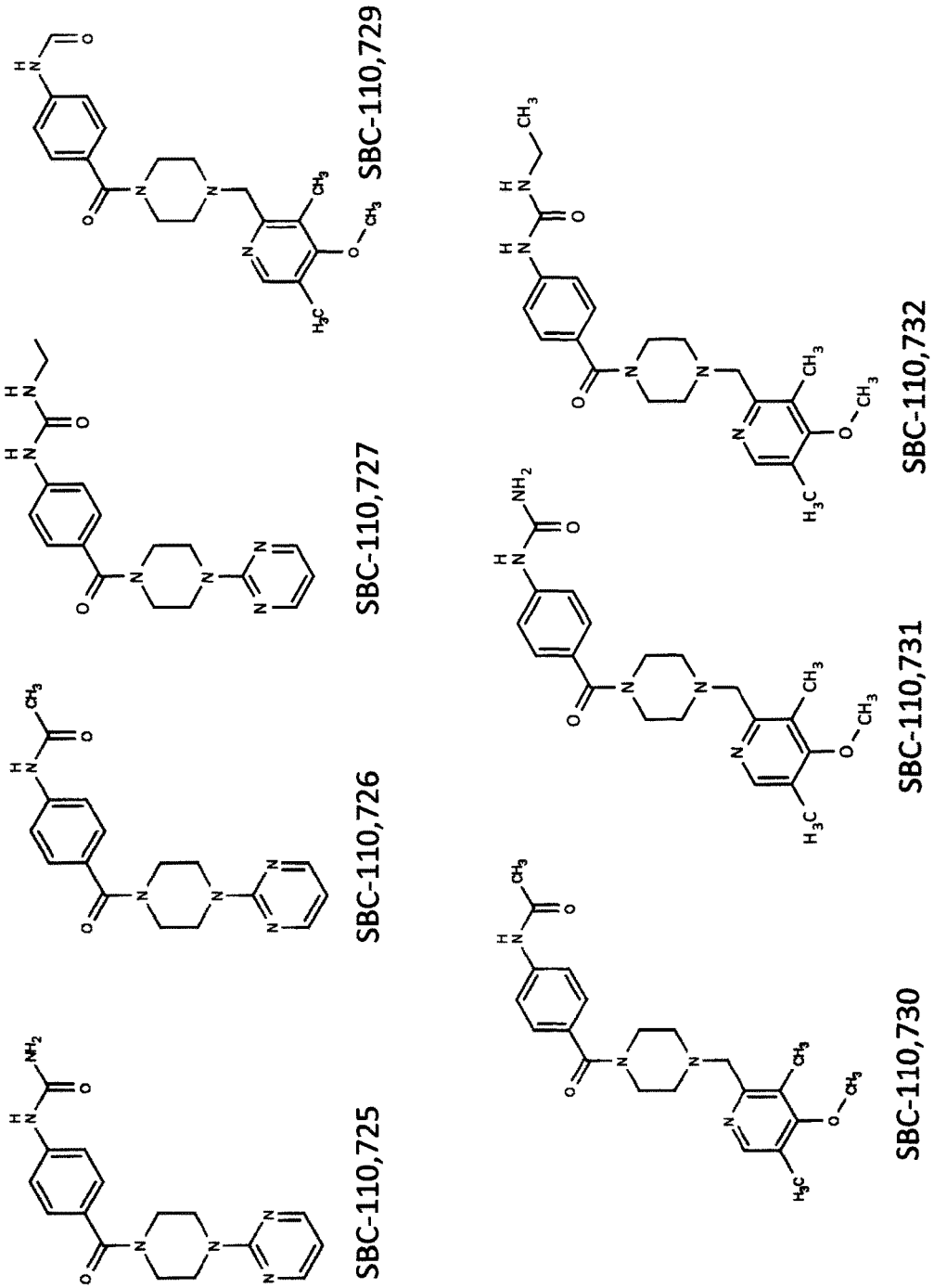
Figure 1:
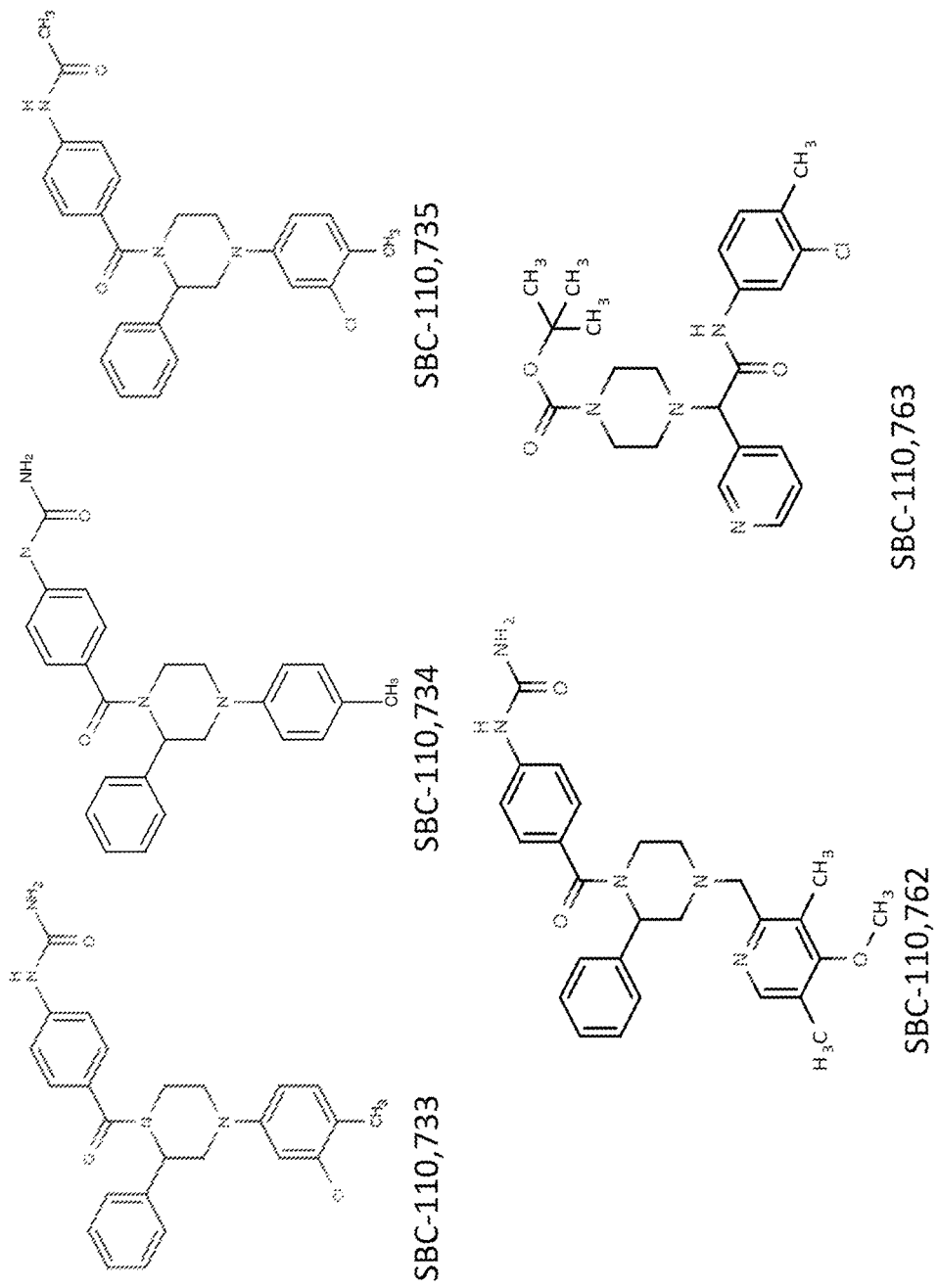
Figure 1:
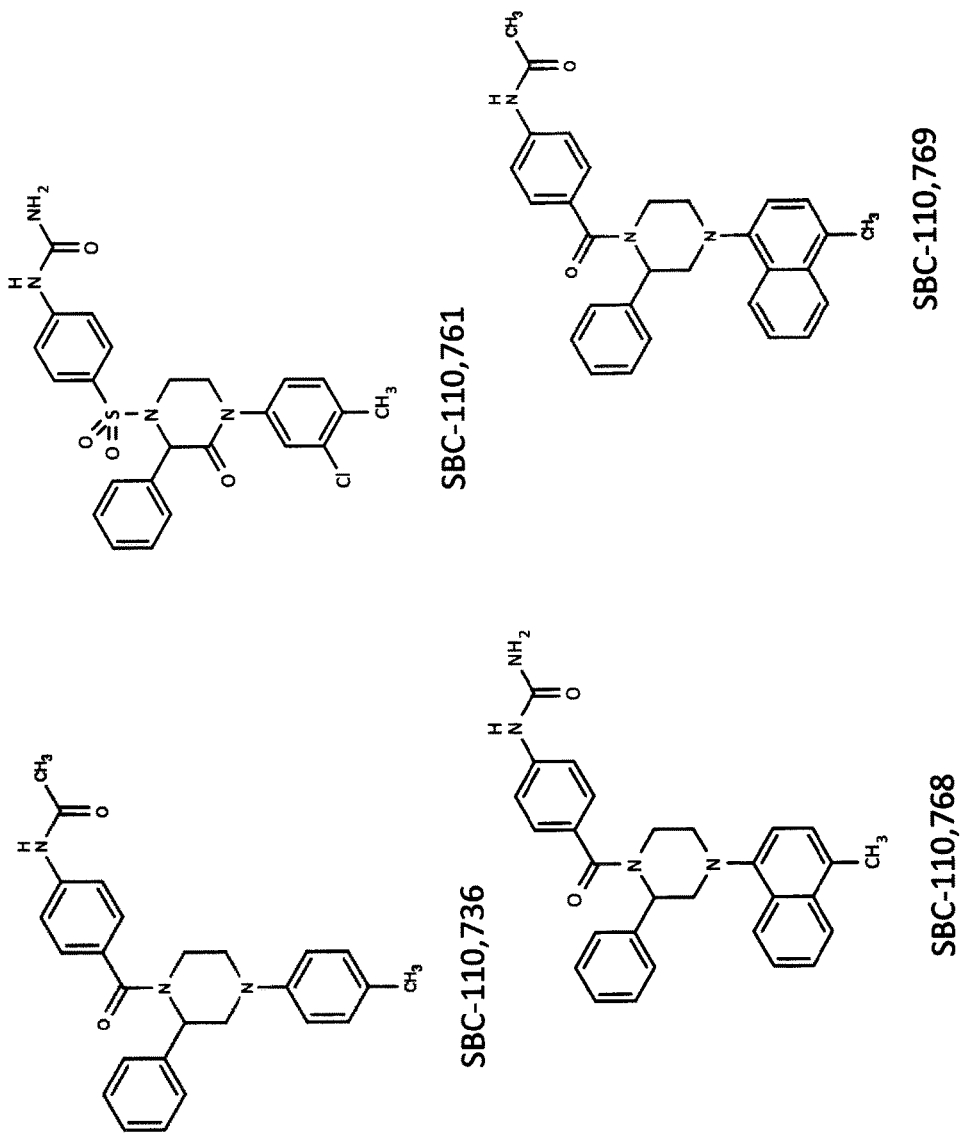
Figure 1:
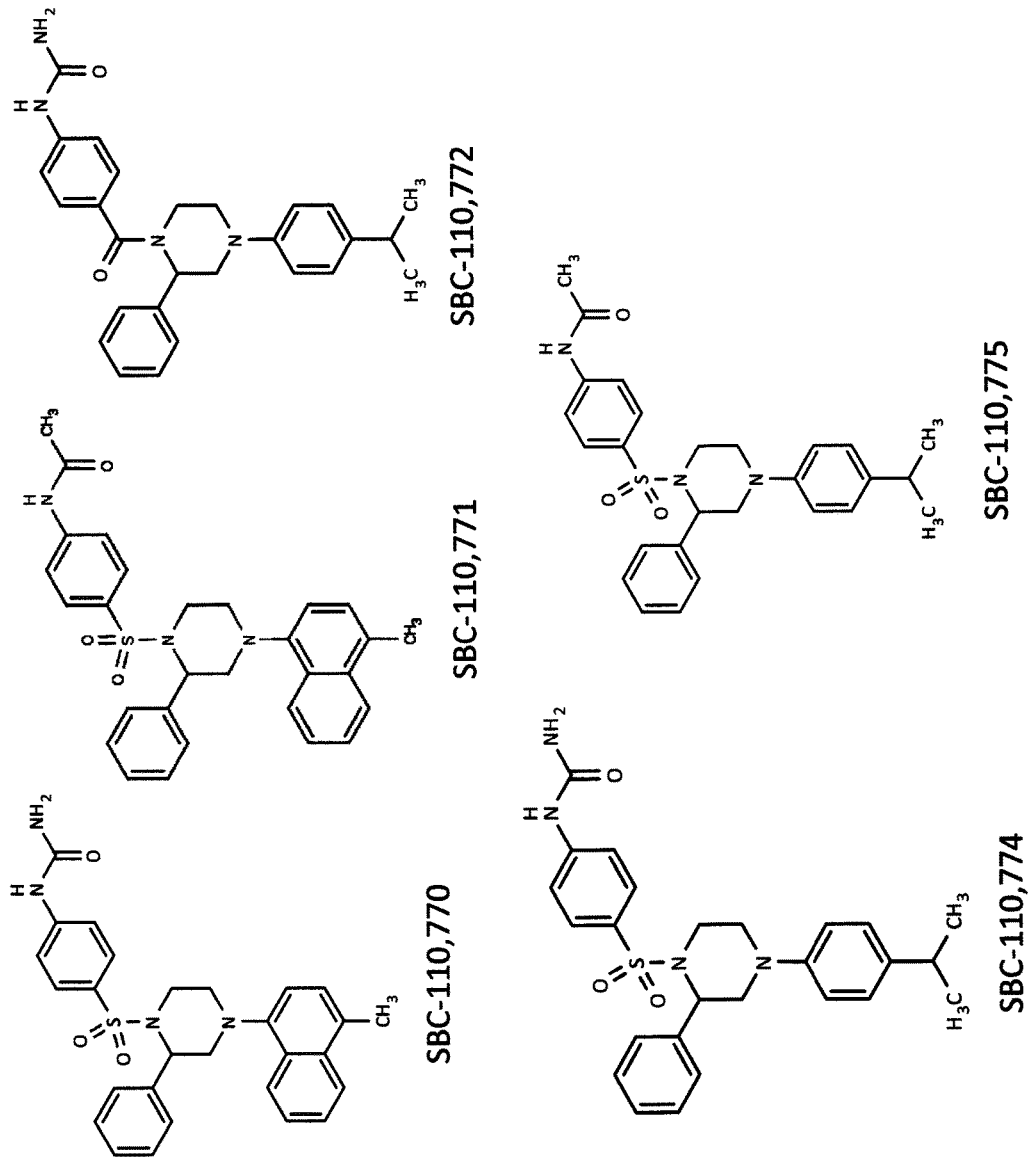
Figure 1:
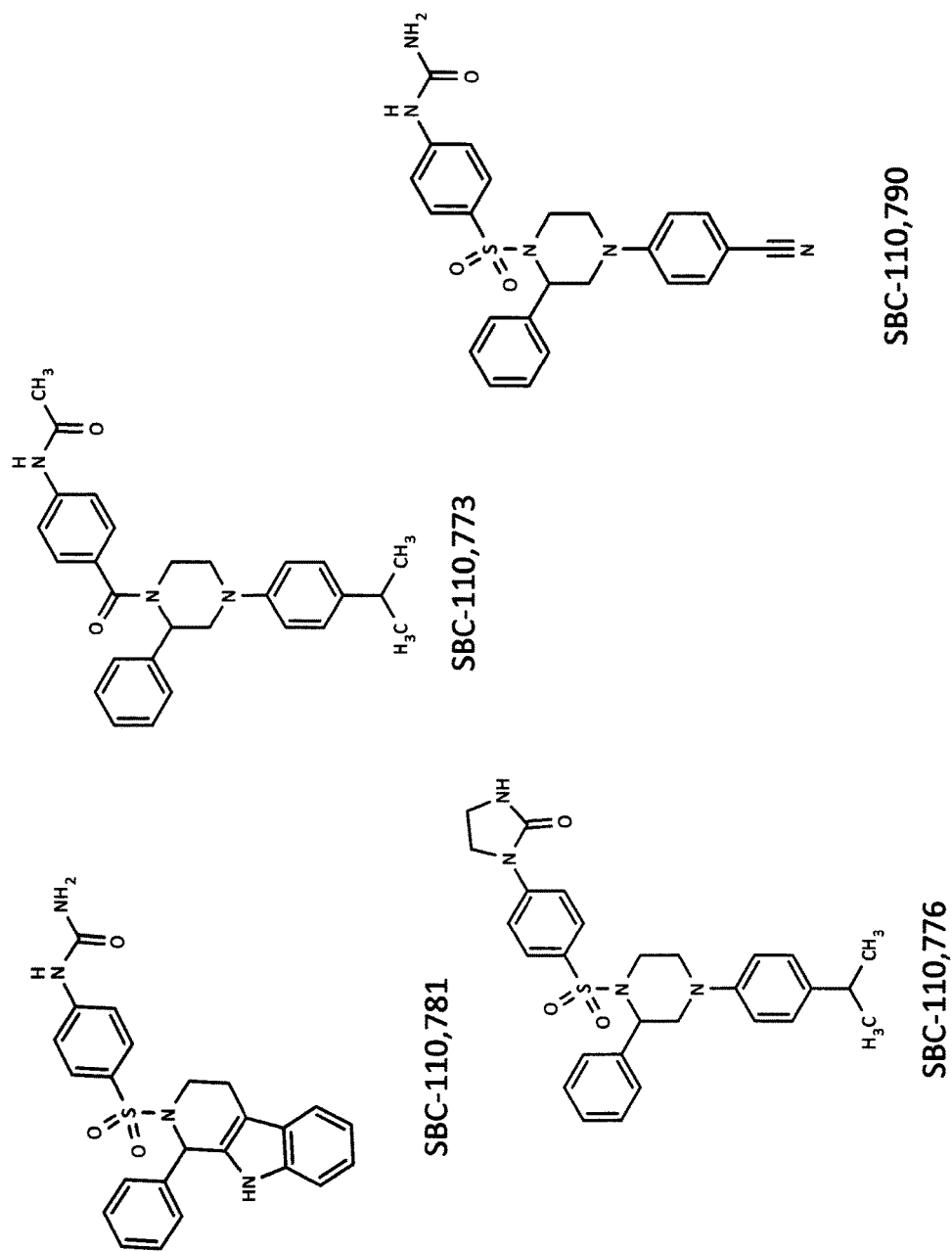

The present invention relates to small molecules that down regulate the function of extracellular proprotein convertase subtilisin kexin type 9 (PCSK9), including its interaction with the low density lipoprotein (LDL) receptor (LDLR), and methods of using these antagonists as a medicament. The small molecule modulators of PCSK9 function can be used therapeutically to lower LDL-cholesterol levels in blood, and can be used in the prevention and/or treatment of cholesterol and lipoprotein metabolism disorders, including familial hypercholesterolemia, atherogenic dyslipidemia, atherosclerosis, and, more generally, cardiovascular disease (CVD).

As used herein, the term "lower alkyl" denotes branched or unbranched hydrocarbon chains, having 1 to about 8 carbons, such as, methyl, ethyl, n-propyl, iso-propyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group optionally substituted with one or more functional groups which are attached commonly to such chains, such as, hydroxy, halogen, mercapto or thio, cyano, alkylthio, carboxy, carbalkoxy, amino, nitro, alkoxy, or optionally substituted, alkenyl, alkynyl, heterocyclyl, aryl, heteroaryl, and the like to form alkyl groups such as trifluoro methyl, 3-hydroxyhexyl, 2-carboxypropyl, 2-fluoroethyl, carboxymethyl, cyanobutyl, phenethyl, benzyl and the like.

The term "halogen" or "halo" as used herein alone or as part of another group refers to chlorine, bromine, fluorine, and iodine.

The term "alkoxy" refers to alkyl-O—, in which alkyl is as defined above.

The term "alkylthio" refers to alkyl-S—, in which alkyl is as defined above.

The terms "amino", "monoalkylamino", "dialkylamino" refers to the moiety —NR'R", in which R' and R", each independently represents H, alkyl or aryl, all as defined herein.

The term "carboxy" refers to the moiety —C(=O)OH.

The term "carbalkoxy" refers to the moiety —C(=O)O-alkyl, in which alkyl is as defined above.

The term "carboxamido" refers to the moiety —C(=O)—NR'R", in which R' and R", each independently represents H, alkyl or aryl, all as defined herein.

The term "amino (monoalkylamino-, dialkylamino-) carbonylamino" refers to the moiety —NHC(=O)NR'R", in which R' and R" each independently represents H, alkyl or aryl, all as defined herein.

The term "carbamato" refers to the moiety —NR'C(=O)OR", in which R' and R", each independently represents H, alkyl or aryl, all as defined herein.

The term "amido" refers to the moiety —NRC(=O)—R", in which R' and R", each independently represents H, alkyl or aryl, all as defined herein.

The term "alkylsulfonyl" refers to the moiety —S(=O)$_2$-alkyl, in which alkyl is as previously defined.

The term "alkylsulfonyloxy" refers to the moiety —OS(=O)$_2$-alkyl, wherein alkyl is as previously defined.

The term "amino(monoalkylamino-, dialkylamino-)sulfinyl" refers to the moiety —S(=O)NR'R" in which R' and R" each independently represents H, alkyl or aryl, all as defined herein.

The term "amino(monoalkylamino-, dialkylamino-)sulfonyl" refers to the moiety —S(=O)$_2$NR'R", in which R' and R" each independently represents H, alkyl or aryl, all as defined herein.

The term "alkylsulfonylamino" refers to the moiety —NHS(=O)$_2$-alkyl, in which alkyl is as previously defined.

The term "hydroxysulfonyloxy" refers to the moiety —OS(=O)$_2$OH.

The term "alkoyxsulfonyloxy" refers to the moiety —OS(=O)$_2$O-alkyl, in which alkyl is as previously defined.

The term "alkylsulfonyloxy" refers to the moiety —OS(=O)$_2$-alkyl, in which alkyl is as previously defined.

The term "hydroxysulfonyl" refers to the moiety —S(=O)$_2$OH.

The term "alkoxysulfonyl" refers to the moiety —S(=O)$_2$O-alkyl, wherein alkyl is as previously defined.

The term "alkylsulfonylalkyl" refers to the moiety -alkyl-S(=O)$_2$-alkyl, wherein alkyl (each instance) is as previously defined.

The term "amino(monoalkylamino-, dialkylamino-)sulfonylalkyl" refers to the moieties -alkyl-S(=O)$_2$—NR'R", wherein alkyl is as previously defined, and R' and R" each independently represents H, alkyl or aryl, all as defined herein.

The term "amino(monoalkylamino-, dialkylamino-)sulfinylalkyl" refers to the moieties -alkyl-S(=O)—NR'R", wherein alkyl is as previously defined, and R' and R" each independently represents H, alkyl or aryl, all as defined herein.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl cyclododecyl and cyclohexenyl.

"Substituted cycloalkyl" includes a cycloalkyl group optionally substituted with 1 or more substituents such as halogen, alkyl, substituted alkyl, alkoxy, hydroxy, aryl, substituted aryl, aryloxy, cycloalkyl, alkylamido, alkanoylamino, oxo, acyl, arylcarbonylamino, amino, nitro, cyano, thiol and/or alkylthio and/or any of the substituents included in the definition of "substituted alkyl."

Unless otherwise indicated, the term "alkenyl" as used herein by itself or as part of another group refers to straight or branched chain of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group optionally substituted with one or more substituents, such as the substituents included above in the definition of "substituted alkyl" and "substituted cycloalkyl."

Unless otherwise indicated, the term "alkynyl" as used herein by itself or as part of another group refers to straight or branched chain of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" includes an alkynyl group optionally substituted with one or more substituents, such as the substituents included above in the definition of "substituted alkyl" and "substituted cycloalkyl."

Unless otherwise indicated, the term "aryl" or "Ar" as employed herein alone or as part of another group refers to monocyclic and polycyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring, such as aryl, cycloalkyl, heteroaryl or cycloheteroalkyl rings or substituted forms thereof.

"Substituted aryl" includes an aryl group optionally substituted with one or more functional groups, such as halo, alkyl, haloalkyl (e.g., trifluoromethyl), alkoxy, haloalkoxy (e.g., difluoromethoxy), alkenyl, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, alkylcarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are optionally substituted alkyl, aryl or any of the other substituents mentioned in the definitions), thiol, alkylthio, arylthio, heteroarylthio, arylthioalkyl, alkoxyarylthio, alkylaminocarbonyl, arylaminocarbonyl, aminocarbonyl, alkylcarbonyloxy, arylcarbonyloxy, amido, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heteroaryl" as used herein alone or as part of another group refers to a 5- or 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophenyl, indolyl), and includes possible N-oxides. "Substituted heteroaryl" includes a heteroaryl group optionally substituted with 1 to 4 substituents, such as the substituents included above in the definition of "substituted alkyl" "substituted cycloalkyl" and "substituted aryl". Substituted heteroaryl also includes fused heteroaryl groups which include, for example, quinoline, isoquinoline, indole, isoindole, carbazole, acridine, benzimidazole, benzofuran, isobenzofuran, benzothiophene, phenanthroline, purine, and the like.

The term "heterocyclo", "heterocycle" or "heterocyclic ring," as used herein alone or as part of another group, represents an unsubstituted or substituted stable 5- to 7-membered monocyclic ring system which may be saturated or partially unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl.

The term "optionally substituted" is used herein to signify that a chemical moiety referred to, e.g., alkyl, aryl, heteroaryl, may be unsubstituted or substituted with one or more groups including, without limitation, lower alkyl, alkenyl, alkynyl, cycloalkyl, arylalkyl, aryl, heterocycle, heteroaryl, hydroxyl, amino, alkoxy, halogen, carboxy, carbalkoxy, carboxamido, amido (including formamido, alkylamido and arylamido), aminocarbonylamino, monoalkylaminocarbonylamino, dialkylaminocarboxylamino, carbamato, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinylalkyl and the like. The chemical moieties of the above-described Formulas I-IX which may be optionally substituted include lower alkyl, alkenyl, alkynyl, cycloalkyl, arylalkyl, aryl, heterocycle, and heteroaryl. For example, optionally substituted alkyl would comprise both propyl and 2-chloro-propyl. Additionally, "optionally substituted" is also inclusive of embodiments where the named substituent or substituents have multiple substituents rather than simply a single substituent. For example, optionally substituted aryl may comprise both phenyl and 3-bromo-4-chloro-6-ethyl-phenyl.

As used herein, the term "subject" includes both humans and animals. As used herein, the term "PCSK9" refers to any form of the protein PCSK9, including PCSK9 mutants and variants, which retain at least part of PCSK9 activity or function. Unless otherwise indicated, such as by specific reference to human PCSK9, PCSK9 refers to all mammalian species of native sequence PCSK9, e.g., human, porcine, bovine, equine, canine and feline. One exemplary human PCSK9 sequence is found as Uniprot Accession Number Q8NBP7 (SEQ ID NO: 1 (FIG. 2)).

As used herein, a "modulator of PCSK9 function" refers to a small molecule that is able to inhibit PCSK9 biological activity or function, and/or downstream pathway(s) mediated by PCSK9 signaling, including PCSK9-mediated down-regulation of the LDLR, and PCSK9-mediated inhibition of the decrease in LDL blood clearance. A modulator of PCSK9 function encompasses compounds that block, antagonize, suppress or reduce (to any degree including significantly) PCSK9 biological activity, including downstream pathways mediated by PCSK9 signaling, such as LDLR interaction and/or elicitation of a cellular response to PCSK9. For purpose of the present invention, it will be explicitly understood that the term "modulator of PCSK9 function" encompasses all the previously identified terms, titles, and functional states and characteristics whereby the PCSK9 itself, a PCSK9 biological activity (including but not limited to its ability to mediate any aspect of interaction with the LDLR, down regulation of LDLR, and inhibit the decrease in blood LDL clearance), or the consequences of the biological activity, are substantially nullified, decreased, or neutralized in any measurable degree. In some embodiments, a modulator of PCSK9 function binds PCSK9 and prevents its interaction with the LDLR or its secretion. In other embodiments, a modulator of PCSK9 function binds to the active site of PCSK9 to stabilize its zymogen and prevent autoprocessing. In further embodiments, a modulator of PCSK9 function decreases or blocks PCSK9 mediated down-regulation of the LDLR; inhibits the PCSK9-mediated decrease in LDL blood clearance; increases LDL clearance in media by cultured hepatocytes; increases blood LDL clearance by the liver in vivo; improves patients' sensitivity to other LDL lowering drugs, including statins; is synergistic to other LDL lowering drugs, including statins; and blocks PCSK9 interaction with other yet to be identified factors. Examples of modulators of PCSK9 function are provided herein.

The compounds used in the method of the invention can be administered as salts, which are also within the scope of this invention. Pharmaceutically acceptable (i.e., non-toxic, physiologically compatible) salts are preferred. If the compounds of the method of the present invention have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid or lysine or arginine, or benzoic acid, or with organic sulfonic acids, such as (C1-C4) alkyl or arylsulfonic acids which are unsubstituted or substituted, for example by halogen, for example methyl- or para-toluene-sulfonic acid. Corresponding acid addition salts can also be formed having plural basic centers, if desired. The compounds used in the method of the present invention having at least one acid group (for example COOH) can also form salts with suitable bases. Representative examples of such salts include metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may also be formed.

Preferred salts of the compounds described herein which contain a basic group include monohydrochloride, hydrogensulfate, methanesulfonate, phosphate or nitrate.

Preferred salts of the compounds described herein which contain an acid group include sodium, potassium and magnesium salts and pharmaceutically acceptable organic amines.

All stereoisomers of the compounds which may be used in the methods described herein, either in a mixture or in pure or substantially pure form, are considered to be within the scope of this invention. The compounds of the present invention can have asymmetric centers at any of the carbon atoms including any one of the R substituents. Consequently, compounds used in the method of the invention can exist in enantiomeric or diastereomeric forms or in mixtures thereof. The processes for preparation of such compounds can utilize racemates, enantiomers or diastereomers as starting materials. When diastereomeric or enantiomeric products are prepared, they can be separated by conventional methods for example, chromatographic, chiral HPLC or fractional crystallization.

As used herein, the term "pharmacophore" refers to the ensemble of steric and electronic features that are necessary to ensure the optimal supramolecular interactions with a specific biological target structure and to trigger, activate, block, inhibit or modulate the biological target's biological activity, as the case may be. See, IUPAC, *Pure and Applied Chemistry* (1998) 70: 1129-1143.

As used herein, the term "pharmacophore model" refers to a representation of points in a defined coordinate system wherein a point corresponds to a position or other characteristic of an atom or chemical moiety in a bound conformation of a ligand and/or an interacting polypeptide, protein, or ordered water molecule. An ordered water molecule is an observable water in a model derived from structural determination of a polypeptide or protein. A pharmacophore model can include, for example, atoms of a bound conformation of a ligand, or portion thereof. A pharmacophore model can include both the bound conformations of a ligand, or portion thereof, and one or more atoms that interact with the ligand and are from a bound polypeptide or protein. Thus, in addition to geometric characteristics of a bound conformation of a ligand, a pharmacophore model can indicate other characteristics including, for example, charge or hydrophobicity of an atom or chemical moiety. A pharmacophore model can incorporate internal interactions within the bound conformation of a ligand or interactions between a bound conformation of a ligand and a polypeptide, protein, or other receptor including, for example, van der Waals interactions, hydrogen bonds, ionic bonds, and hydrophobic interactions. A pharmacophore model can be derived from two or more bound conformations of a ligand.

As used herein, the term "ligand" refers to any compound, composition or molecule that interacts with the ligand binding domain of a receptor and modulates its activity. A "ligand" may also include compounds that modulate the receptor without binding directly to it.

In carrying out the method of the invention, the above-described compounds may be administered as such, or in a form from which the active agent can be derived, such as a prodrug. A prodrug is a derivative of a compound described herein, the pharmacologic action of which results from the conversion by chemical or metabolic processes in vivo to the active compound. The term "prodrug esters" as employed herein includes esters and carbonates formed by reacting one or more hydroxyls of compounds used in the method of the invention with alkyl, alkoxy, or aryl substituted acylating agents employing procedures known to those skilled in the art to generate acetates, pivalates, methylcarbonates, benzoates and the like. Any compound that can be converted in vivo to provide the bioactive agent (i.e., a compound of formula I) is a prodrug within the scope and spirit of the invention. Various forms of prodrugs are well known in the art. A comprehensive description of prodrugs and prodrug derivatives are described in: (a) The Practice of Medicinal Chemistry, Camille G. Wermuth et al., Ch 31, (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., Ch. 5, pgs, 113-191 (Harwood Academic Publishers, 1991).

The therapeutic agent used in practicing the method of the invention is administered in an amount sufficient to induce the desired therapeutic effect in the recipient thereof. Thus the term "therapeutically effective amount" as used herein refers to an amount of a therapeutic agent which is sufficient to treat or prevent a condition treatable by administration of one or more of the compounds of Formulas I-IX, above, or a prodrug thereof. Preferably, the therapeutically effective amount refers to the amount appropriate to treat a PCSK9-associated condition, i.e. to bring about a detectable therapeutic or preventative or ameliorative effect. The effect may include, for example, treatment or prevention of the conditions described herein.

The compound(s) described herein may be administered at a dose in range from about 0.01 mg to about 200 mg/kg of body weight per day. A dose of from 0.1 to 100, and preferably from 1 to 30 mg/kg per day in one or more applications per day should be effective to produce the desired result. By way of example, a suitable dose for oral administration would be in the range of 1-30 mg/kg of body weight per day, whereas a typical dose for intravenous administration would be in the range of 1-10 mg/kg of body weight per day. Of course, as those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

The compounds used in the method of the invention will typically be administered from 1-4 times a day, so as to deliver the above-mentioned daily dosage. However, the exact regimen for administration of the compounds described herein will necessarily be dependent on the needs of the individual subject being treated, the type of treatment administered and the judgment of the attending medical specialist.

In one aspect, the invention provides a method for treating or preventing hypercholesterolemia, and/or at least one symptom of dyslipidemia, atherosclerosis, CVD or coronary heart disease, in an individual comprising administering to the individual an effective amount of a modulator of PCSK9 function that antagonizes circulating PCSK9.

In a further aspect, the invention provides an effective amount of a modulator of PCSK9 function that antagonizes circulating PCSK9 for use in treating or preventing hypercholesterolemia, and/or at least one symptom of dyslipidemia, atherosclerosis, CVD or coronary heart disease, in an individual. The invention further provides the use of an effective amount of a modulator of PCSK9 function that antagonizes extracellular or circulating PCSK9 in the manufacture of a medicament for treating or preventing hypercholesterolemia, and/or at least one symptom of dyslipidemia, atherosclerosis, CVD or coronary heart disease, in an individual.

The methods of the invention use a modulator of PCSK9 function, which refers to any molecule that blocks, suppresses or reduces (including significantly reduces) PCSK9 biological activity, including downstream pathways mediated by PCSK9 signaling, such as elicitation of a cellular response to PCSK9.

A modulator of PCSK9 function should exhibit any one or more of the following characteristics: (a) bind to PCSK9; (b) decrease or block PCSK9 interaction with the LDLR; (c) decrease or block secretion of PCSK9; (d) decrease or block PCSK9 mediated down-regulation of the LDLR; (e) inhibit the PCSK9-mediated decrease in LDL blood clearance, (f) increase LDL clearance in media by cultured hepatocytes, (g) increase blood LDL clearance by the liver in vivo, (h) improve patients' sensitivity to other LDL lowering drugs, including statins, (i) is synergistic to other LDL lowering drugs, including statins; and (j) block PCSK9 interaction with other yet to be identified factors.

In general, the compound(s) used in the method of the invention can be administered to achieve modulation of PCSK9 function by using any acceptable route known in the art, either alone or in combination with one or more other therapeutic agents. Thus, the active agent(s) can be administered orally, buccally, parenterally, such as by intravenous or intra-arterial infusion, intramuscular, intraperitoneal, intrathecal or subcutaneous injection, by lipo some-mediated delivery, rectally, vaginally, by inhalation or insufflation, transdermally or by otic delivery.

The orally administered dosage unit may be in the form of tablets, caplets, dragees, pills, semisolids, soft or hard gelatin capsules, aqueous or oily solutions, emulsions, suspensions or syrups. Suitable dosage forms for parenteral administration include injectable solutions or suspensions, suppositories, powder formulations, such as microcrystals or aerosol spray. The active agent may also be incorporated into a conventional transdermal delivery system.

As used herein, the expression "physiologically compatible carrier medium" includes any and all solvents, diluents, or other liquid vehicle, dispersion or suspension aids, surface agent agents, isotonic agents, thickening or emulsifying agents, preservatives, solid binders, lubricants, fillers and the like as suited for the particular dosage form desired. Remington: The Science and Practice of Pharmacy, $20^{th}$ edition, (A. R. Genaro et al., Part 5, Pharmaceutical Manufacturing, pp. 669-1015 (Lippincott Williams & Wilkins, Baltimore, Md./Philadelphia, Pa.) (2000)) discloses various carriers used in formulating pharmaceutical compositions and known techniques for the preparation thereof. Except insofar as any conventional pharmaceutical carrier medium is incompatible with the PCSK9 modulators used in the present invention, such as by producing an undesirable biological effect or otherwise interacting in an deleterious manner with any other component(s) of a formulation comprising such compounds, its use is contemplated to be within the scope of this invention.

For the production of solid dosage forms, including hard and soft capsules, the therapeutic agent may be mixed with pharmaceutically inert, inorganic or organic excipients, such as lactose, sucrose, glucose, gelatine, malt, silica gel, starch or derivatives thereof, talc, stearic acid or its salts, dried skim milk, vegetable, petroleum, animal or synthetic oils, wax, fat, polyols, and the like. For the production of liquid solutions, emulsions or suspensions or syrups one may use excipients such as water, alcohols, aqueous saline, aqueous dextrose, polyols, glycerine, lipids, phospholipids, cyclodextrins, vegetable, petroleum, animal or synthetic oils. For suppositories one may use excipients, such as vegetable, petroleum, animal or synthetic oils, wax, fat and polyols. For aerosol formulations, one may use compressed gases suitable for this purpose, such as oxygen, nitrogen and carbon dioxide. The pharmaceutical composition or formulation may also contain one or more additives including, without limitation, preservatives, stabilizers, e.g., UV stabilizers, emulsifiers, sweeteners, salts to adjust the osmotic pressure, buffers, coating materials and antioxidants.

The present invention further includes controlled-release, sustained-release, or extended-release therapeutic dosage forms for administration of the active agent, which involves incorporation of the active agent into a suitable delivery system. This dosage form controls release of the active agent(s) in such a manner that an effective concentration of the active agent(s) in the bloodstream may be maintained over an extended period of time, with the concentration in the blood remaining relatively constant, to improve therapeutic results and/or minimize side effects. Additionally, a controlled-release system would provide minimum peak to trough fluctuations in blood plasma levels of the active agent.

In pharmaceutical compositions used in practicing the method of the invention, the active agent(s) may be present in an amount of at least 0.5 and generally not more than 95% by weight, based on the total weight of the composition, including carrier medium and/or supplemental active agent(s), if any. Preferably, the proportion of active agent(s) varies between 30-90% by weight of the composition.

Preferred compounds for use in practicing this invention include those of Formulas II and VI, above. More preferred compounds are those of Formulas III-V and VII, above. Most preferred are the compounds set out in FIG. 1.

The methods of the present invention will normally include medical follow-up to determine the therapeutic or prophylactic effect brought about in the subject undergoing treatment with the compound(s) and/or composition(s) described herein.

The activities of compounds described herein have been experimentally demonstrated. The following examples are provided to describe the invention in further detail. These examples are provided for illustrative purposes only and are not intended to limit the invention in any way.

Example 1

Test for Secreted PCSK9

Figure 3:
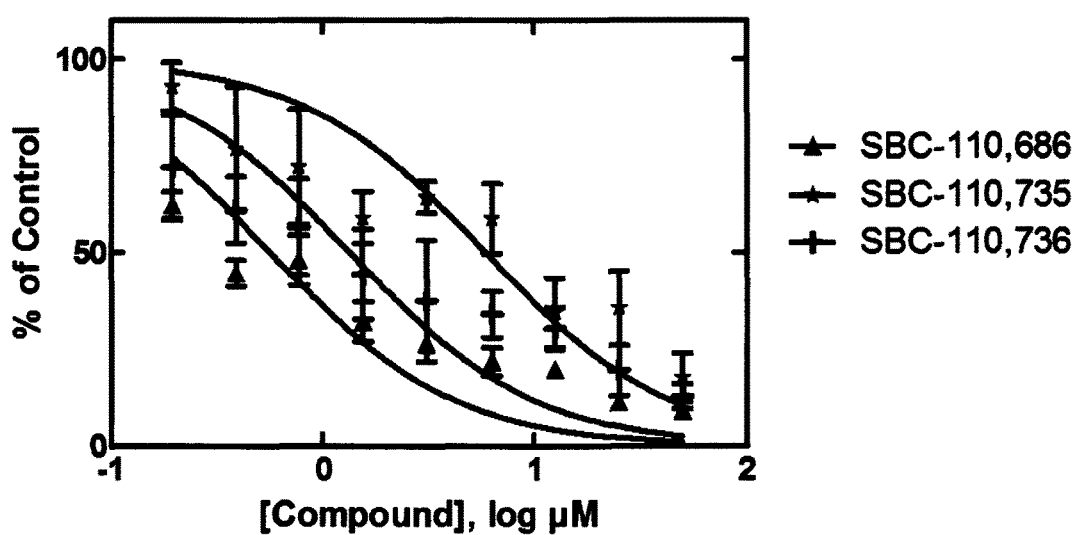

HEK-293T cells were seeded into 96-well plates in a DMEM containing 10% Fetal Bovine Serum media and incubated overnight at 37° C. Cells were transfected with PCSK9 cDNA construct. Compounds at different concentrations were added, followed by additional 43 hours of incubation. Prior to the PCSK9 assay, the cell media was replaced with the DMEM serum free media containing the same concentration of compounds or vehicle, and incubated for additional 5 hrs. The cell media was analyzed for PCSK9 secretion using western blot analysis, imaged and quantitated using a LAS-4000 (GE). Results from selected compounds are shown in FIG. 3.

Example 2

Test for LDLR Upregulation

Figure 4:
Figure 5:
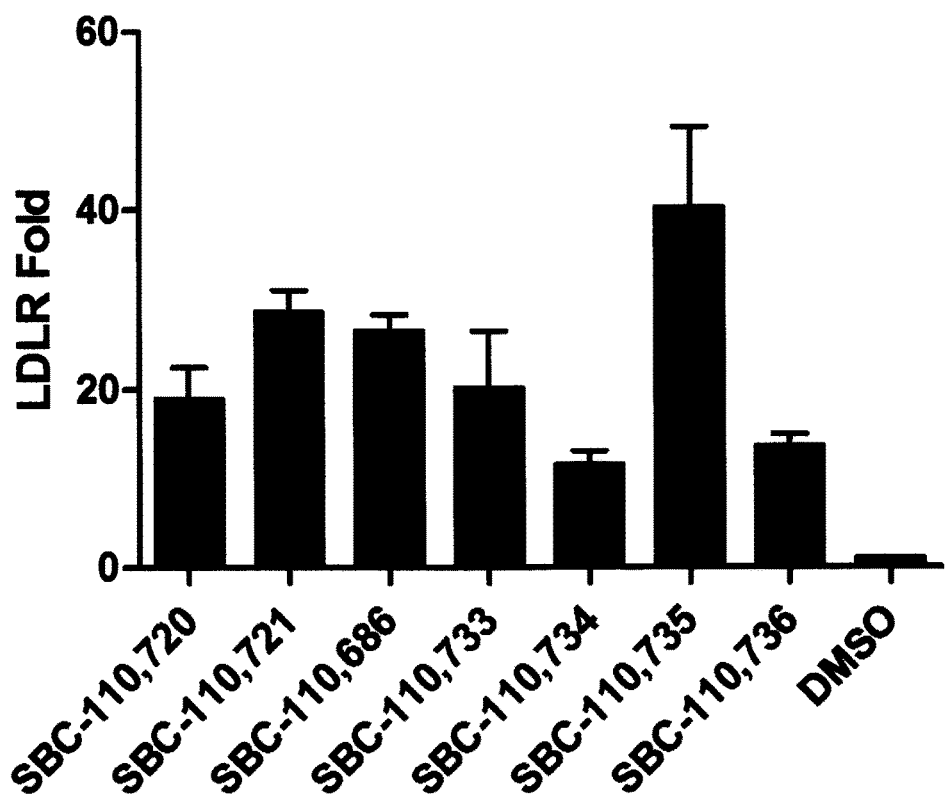

A proprietary recombinant assay was used to demonstrate that co-expression of PCSK9 and LDLR DNA in HEK-293 cells results in a decrease in the expression level of intracellular LDLRs. The present inventors constructed the expression vector of human LDLR under the control of the cytomegalovirus promoter-enhancer (pCMV-LDLR). In addition, a construct containing the PCSK9 (pCMV-PCSK9-FLAG) was made. These constructs were used to transfect mammalian cells and both cell lysate and supernatant were subjected to SDS-PAGE and immunoblot analysis using an anti-PCSK9 or LDLR antibody. The data from the blot showed that cells that were transfected with only pCMV-PCSK9-FLAG expressed both the unprocessed (cells) and processed (media) PCSK9 (FIG. 4). Cells that were transfected with only pCMV-LDLR showed expression of the LDLR in the cells (FIG. 4). However, cells that were transfected with both pCMV-PCSK9-FLAG and pCMV-LDLR showed disappearance of the intracellular LDLR band (FIG. 4), which provides further evidence that the presence of PCSK9 results in degradation of LDLR or chaperon it to the degradation pathway. Addition of inhibitors of PCSK9 processing to the latter cells should result in decreased degradation of the LDLR and the appearance of the 160K Dalton band on the gel. Using this assay, we tested our compounds for their ability to reduce the degradation of the LDLR. HEK-293 cells were used in this assay. They were grown in 96-well plates overnight, and transfected with LDLR/PCSK9. Compounds dissolved in DMSO or vehicle were added to the culture media, and incubated for 24-48 hours; cells will then be lysed. Cell lysate were subjected to quantitation using the above immunoassay. Compounds that inhibit the secretion of the PCSK9 into the media and increase the upregulation of LDLR were selected (FIG. 5).

Figure 6:
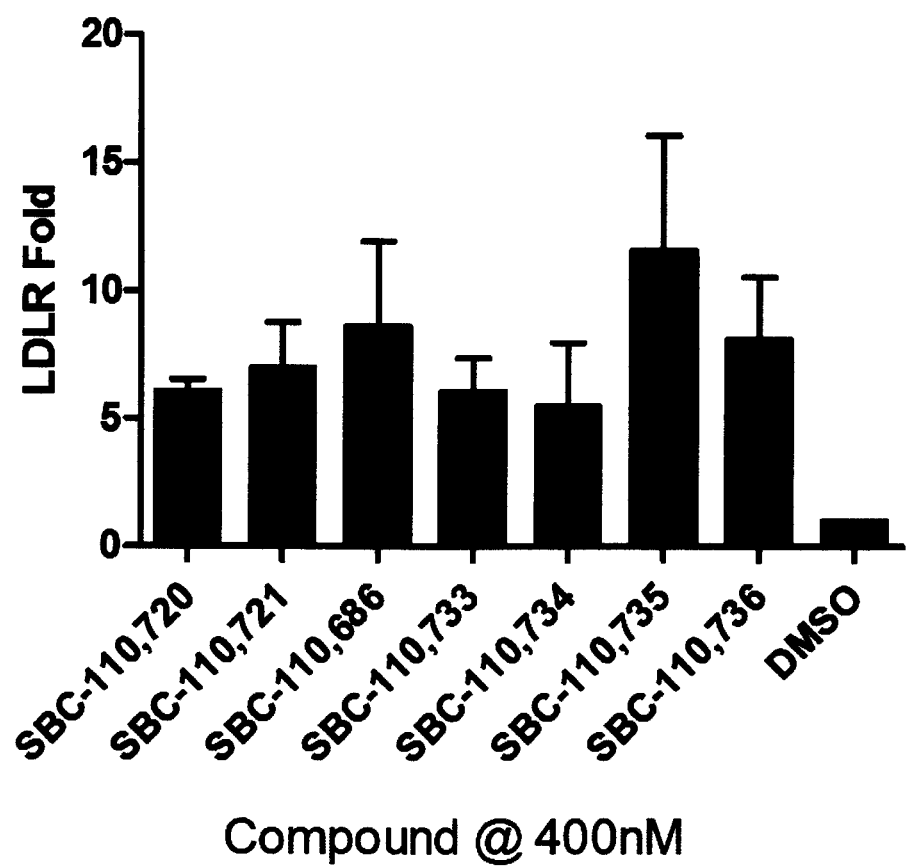

Testing confirmed that compounds described herein are capable of up regulating the endogenously expressed LDLR in HepG2 cells. HepG2 transfected with PCSK9 cells were cultured in 96-well plates at a density of 30,000 cells per well. The next day, cells are treated with selected screening compounds or vehicle. Cells were incubated for 48 hrs and then subjected to quantitation using an LDL receptor-polyclonal antibody and analyzed as described above. The data in FIG. 5 show that these compounds exhibited an increase in the level of LDLR as compared to cells treated with same volume of DMSO with several fold upregulation of LDLR at 0.4 uM as compared to control. Thus, the data support our initial hypothesis in that an inhibition of the processing and secretion of the PCSK9 results in the upregulation of the LDLR (FIG. 6).

Example 3

Uptake of Dil-LDL in HepG2 Cells In Situ

Figure 7:
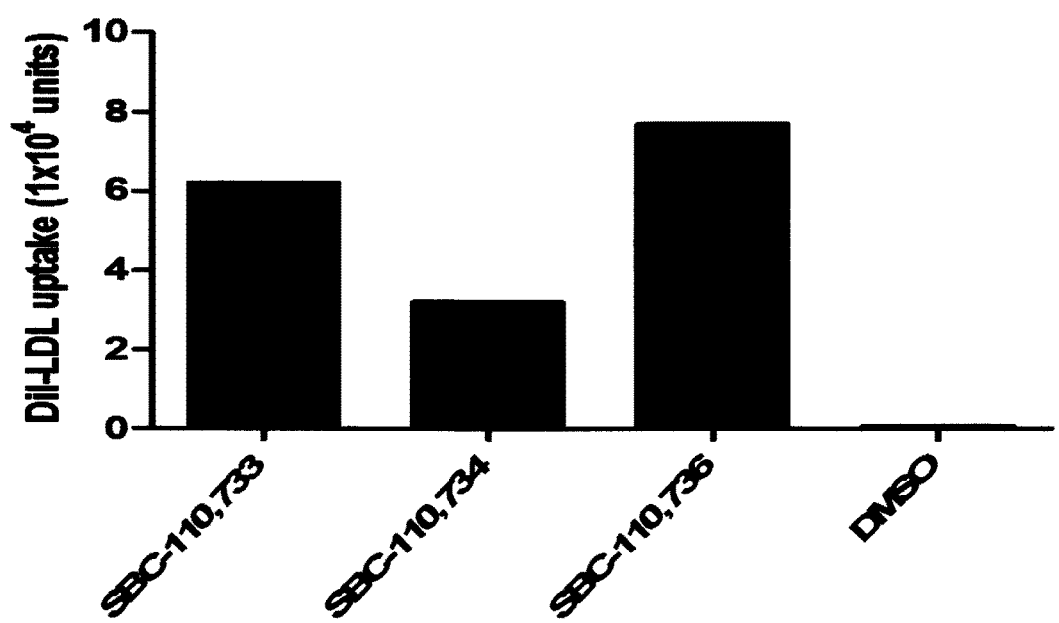

We also tested the ability of the PCSK9 modulator compounds to enhance the uptake of Fluorescent DilLDL in HepG2 cells. Briefly, HepG2 cells were plated and allowed to grow overnight. Compounds were added to the cells followed by the addition of Fluorescent Dil-LDL. Cells were washed extensively, and the Fluorescent Di-LDL taken by the cells were measured using the Synergy 2 plate reader (FIG. 7).

Example 4

Test for Cell Viability

All compounds that inhibit PCSK9 secretion will be used to test for in situ cell viability. HEK-293T cells or HepG2 cells were seeded in 96-well plates in a cell media containing 10% Fetal Bovine Serum and incubated overnight at 37° C. Compounds at various concentrations will be added to cells after 24 hours and incubated for an additional 48 hours. Cell viability was assayed using Resazurin (Sigma 199303) and a Senergy 2 Multi-label plate reader.

Example 5

General Procedures for Synthesis of Compounds of the Formula III-VIII

Figure 8:
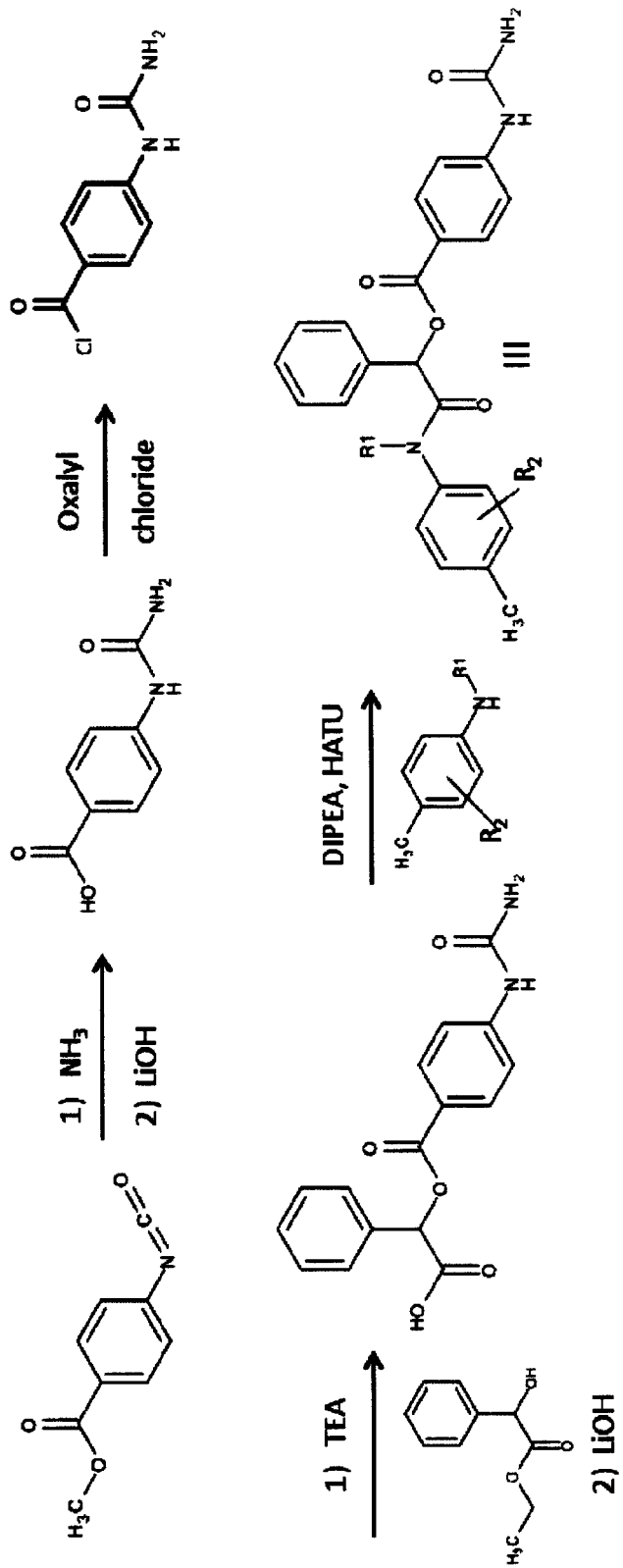

Compounds of the Formula III. General Procedure for the Preparation of Compounds of the Formula III (FIG. 8).

Commercial methyl 4-isocyanatobenzoate is reacted with ammonia (slight excess), then after saponification with LiOH (1.5 equivalents), the crude acid is directly converted to an acid chloride with oxalyl chloride (1.5 equivalents) which is advanced to the next step without purification. The acid chloride is coupled under basic conditions (TEA, 2.0 equivalents) with commercial ethyl mandelate (1.5 equivalents) and, after a second saponification with LiOH (3.0 equivalents), the resulting acid is coupled with substituted anilines (2-5 equivalents) utilizing DIPEA and HATU. After aqueous workup, the resulting residue was subject to flash chromatography using a MeOH gradient (0-10%) in dichloromethane or reverse phase chromatography (Acetonitrile/water 5-95%) to afford the target compounds of the Formula III (e.g., SBC-110,686, FIG. 1).

Compounds of the Formula IV and V. N-Boc-Phenylglycine (Compound 2, FIG. 9) was Prepared According to the Literature.[1]

General procedure for the preparation of compound 3 (FIG. 9): N-Boc-Phenylglycine (cmpd 1; 1 equivalent), the corresponding aniline (1.2 equivalents), N,N-Diisopropylethylamine (5 equivalents) and HATU (O-(7-azabenzotriazol-1-yl)-N,N,N',N'-tetramethyluronium hexafluorophosphate, 1.5 equivalents) were stirred over night at room temperature in DMF (dimethylformamide, 1M solution in the starting material). Following aqueous work up, dichloromethane extraction and evaporation of volatiles, the crude material was flash chromatographed on silica gel columns, using ethyl acetate gradient in hexanes. The resulting N-Boc-amine was stirred at room temperature in dichloromethane (0.5M) and excess trifluoroacetic acid (15 equivalents). After removing volatiles the resulting intermediate amine was advanced to the next step without further purification.

[1] *Organic Letters*, 2004, 6(21), 3675-3678

General procedure for the preparation of intermediates 5 and 6 (FIG. 9): Intermediate amine; 3 was stirred over night at room temperature in dichloromethane with N,N-Diisopropylethylamine (5 equivalents) and 4-nitrobenzoyl chloride (1.2 equivalents) or 4-nitrobenzenesulfonyl chloride (1.2 equivalents) respectively. Aqueous workup was followed by dichloromethane extraction and removal of volatiles. Without further purification, the crude intermediates were diluted in methanol (0.05M) and aqueous 6N hydrochloric acid solution (10% by volume to the methanol). Hydrogenation was done overnight under hydrogen atmosphere over Pd/C (10%, 0.1 equivalents). The reaction mixture was filtered over Celite® and removal of volatiles afforded crude intermediates 5 and 6 which were advanced to the next step without further purification.

Figure 10:
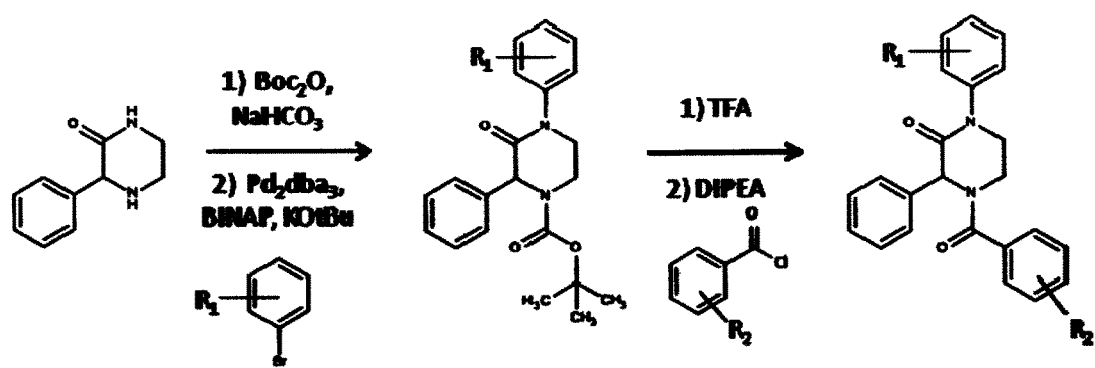

Compounds of the Formula VI. General Procedure for the Preparation of Compounds of the Formula VI (FIG. 10).

Commercial 3-phenyl-piperazin-2-one was protected with Boc$_2$O (1.5 equivalents). After purification, N-arylation was achieved through a cross-coupling reaction with an aryl bromide (1.2 equivalents), Pd$_2$dba$_3$(tris(dibenzylideneacetone)dipalladium(0), 0.2 equivalents), BINAP (2,2'-bis(diphenylphosphino)-1,1'-binaphthyl, 0.2 equivalents), and KOtBu (1.5 equivalents) that were stirred in toluene (0.5M) at 80° C. for 2 hours. After aqueous workup and extraction with dichloromethane, the resulting mixture was flash chromatographed on silica gel using an ethyl acetate gradient (0-15%) in hexanes, to afford N-aryl piperazinones. After Boc removal (TFA, dichloromethane), the amines were advanced without further purification. Reaction of the resulting amines with available or synthesized benzoyl chlorides or arylsulfonyl chloride derivatives provided, after aqueous workup, a residue that was subject to flash chromatography using a MeOH gradient (0-5%) in dichloromethane or reverse phase chromatography (Acetonitrile/water 5-95%) to afford the target compounds of the Formula VI.

Compounds of the Formula VII and VIII.

Figure 11:
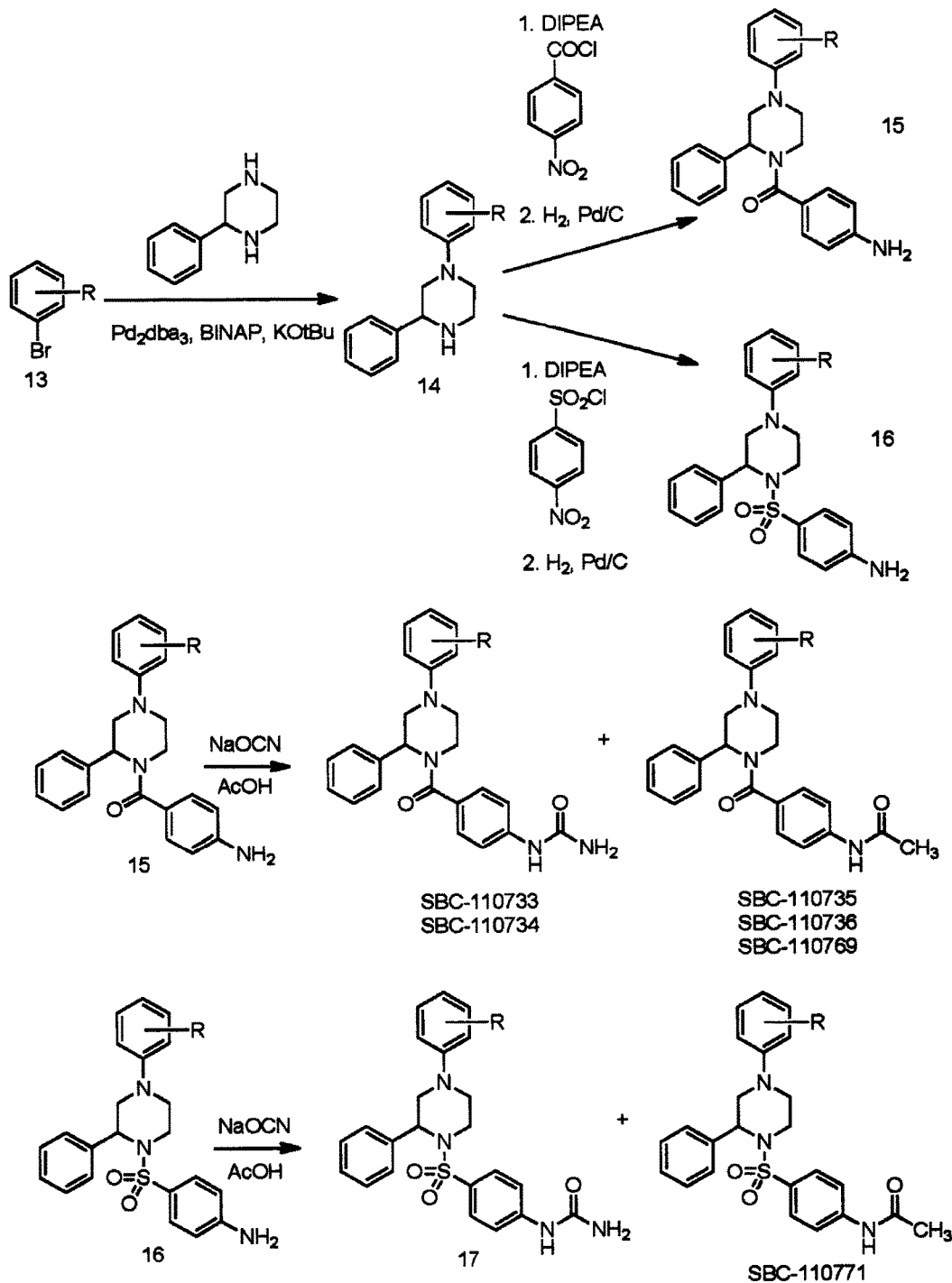

Procedure for the preparation of piperazine 14 (FIG. 11). Commercially available 2-phenyl-piperazine (I equivalent), phenyl bromides 13 (1.1 equivalents), Pd$_2$dba$_3$ tris(dibenzylideneacetone)dipalladium(0), 0.2 equivalents), BINAP (2,2'-bis(diphenylphosphino)-1,1'-binaphthyl, 0.2 equivalents) and KOtBu (1.5 equivalents) were stirred in toluene (0.5M) at 80° C. for 2 hours. After aqueous workup and extraction with dichloromethane, the resulting mixture was flash chromatographed on silica gel using an ethyl acetate gradient (0-25%) in hexanes, to afford N-substituted piperazine 14.

General procedure for the preparation of intermediates 8 (FIG. 12), 11 (FIG. 13) and 15 and 16 (FIG. 11); Piperazines 7, 10 and 14 were stirred over night at room temperature in dichloromethane with N,N-Diisopropylethylamine (5 equivalents) and 4-nitrobenzoyl chloride (1.2 equivalents) or 4-nitrobenzenesulfonyl chloride (1.2 equivalents), respectively. Aqueous workup was followed by dichloromethane extraction and removal of volatiles. Without further purification, the crude intermediates were diluted in methanol (0.05M) and aqueous 6N hydrochloric acid solution (10% by volume to the methanol). Hydrogenation was done overnight under hydrogen atmosphere over Pd/C (10%, 0.1 equivalents). The reaction mixture was filtered over Celite® and removal of volatiles afforded crude intermediates 8, 11, 15 and 16 which were advanced to the next step without further purification.

General procedure for the preparation of SBC-110,716, SBC-110,717, SBC-110,728, SBC-110,725, SBC-110,726, SBC-110,729, SBC-110,730, SBC-110,733, SBC-110,734, SBC-110,735, SBC-110,736, SBC-110,769, and SBC-110,771: Intermediates 5, 6, 8, 11, 15 and 16 were stirred overnight with NaOCN (2 equivalents) in acetic acid and water (10:1, 0.05-0.1M). The reaction mixture was transferred to loose silica gel and volatiles were removed and the residue dissolved in DMSO. Flash chromatography using a MeOH gradient (0-10%) in dichloromethane or reverse phase chromatography (Acetonitrile/water 5-95%) afforded the target compounds.

Example 6

Synthesis of SBC-110,716, SBC-110,717 and SBC-110,728

Figure 9:
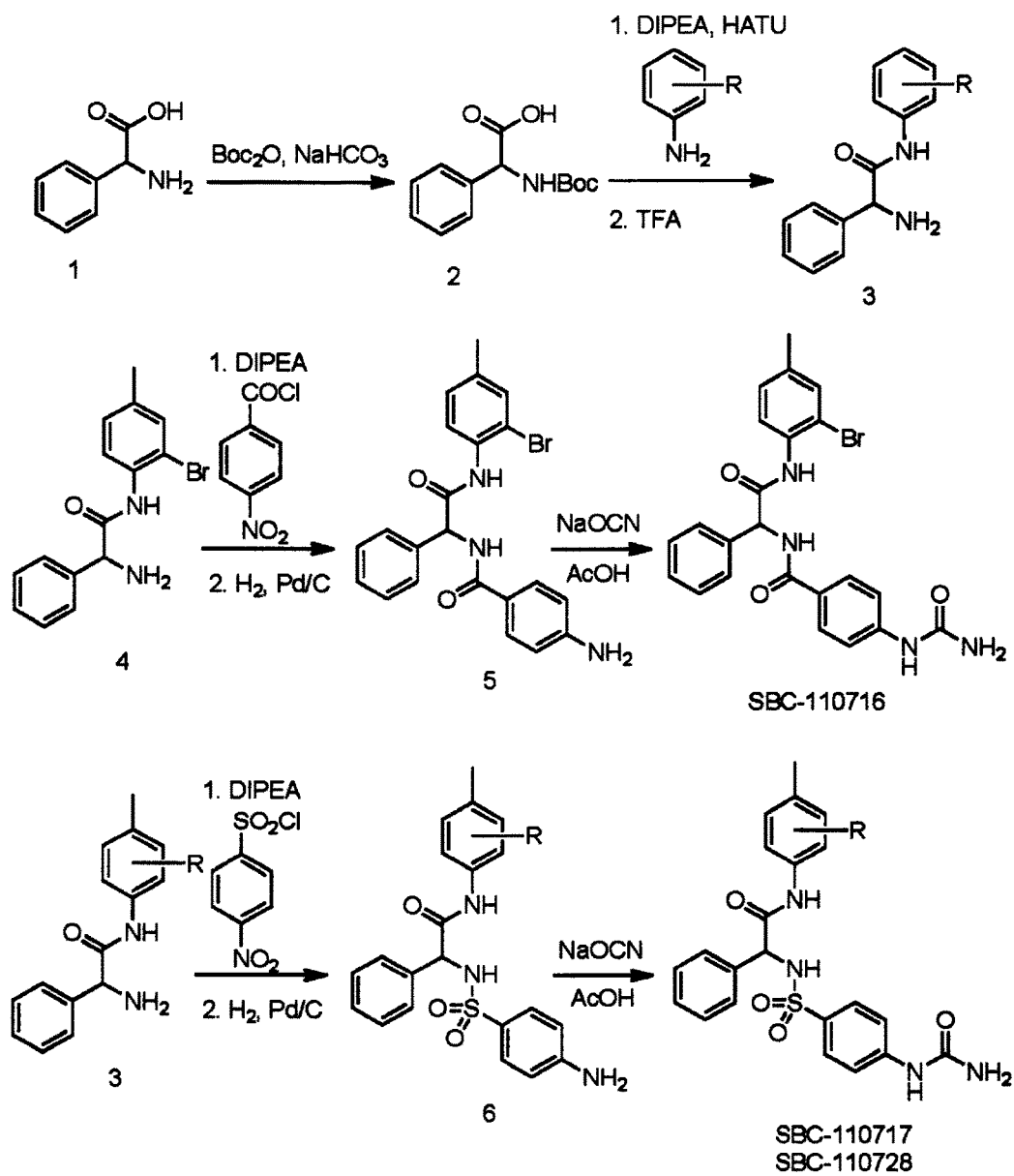

2-Amino-N-(3-chloro-4-methylphenyl)-2-phenylacetamide (compound 3, FIG. 9; R=3-Cl-4-Me): N-Boc-Phenylglycine (1.73 g, 6.90 mmol), 3-Cl-4-Me-aniline (1.00 mL, 8.28 mmol), diisopropylethylamine (6.00 mL, 34.5 mmol) and HATU (3.9 g, 10.35 mmol) were stirred over night in DMF (5 mL) at room temperature. Aqueous work up was followed by dichloromethane extraction and removal of volatiles. Flash chromatography using ethyl acetate gradient (0-35%) in hexanes afforded 1.34 g N-Boc protected amine. The compound was stirred overnight with trifluoroacetic acid (5 mL, excess) in dichloromethane (5 mL). Removal of volatiles afforded 0.99 g of amine 3 (R=3-Cl-4-Me) (97%) which was advanced to the next step without further purification. $^1$H-NMR (DMSO-d6, 400 MHz, δ ppm) 10.77 (s, 1H), 8.77 (s, 1H), 7.75 (d, J=2 Hz, 1H), 7.59-7.57 (m, 2H), 7.51-7.45 (m, 3H), 7.36 (dd, J=8.4, 2 Hz, 1H), 7.31 (d, J=8.4 Hz, 1H), 5.10 (s, 1H), 2.27 (s, 3H).

4-amino-N-(2-((2-bromo-4-methylphenyl)amino)-2-oxo-1-phenylethyl)benzamide (5): 2-amino-N-(2-bromo-4-methylphenyl)-2-phenylacetamide (0.1 g, 0.31 mmol), diisopropylethylamine (0.13 mL, 0.93 mmol) and 4-nitrobenzoylchloride (0.07 g, 0.37 mmol) were stirred overnight in DCM (3 mL). Aqueous work up and dichloromethane extraction were followed by flash chromatography using ethyl acetate gradient (0-15%) in hexanes, affording 0.06 g (41%) of the intermediate compound. The intermediate and Pd/C-10% (0.05 g) in methanol (5 mL) and HO aqueous 6N solution (0.5 mL) were stirred overnight under hydrogen. The reaction mixture was filtered over Celite and volatiles were removed. The crude product 0.058 g (quantitative yield) was advanced to the next step without further purification. $^1$H-NMR (CD$_3$OD, 400 MHz, δ ppm) 7.91 (d, J=8.8 Hz, 2H), 7.49-7.47 (m, 2H), 7.34-7.25 (m, 7H), 7.00 (d, J=8 Hz, 2H), 5.71 (s, 1H), 2.18 (s, 3H). See general procedure (Example 5) for sodium cyanate reaction.

SBC-110,716: $^1$H-NMR (CD$_3$OD, 400 MHz, δ ppm) 7.73 (d, J=6.8 Hz, 2H), 7.48 (d, J=7.6 Hz, 2H), 7.40 (d, J=6.8 Hz, 2H), 7.35-7.25 (m, 5H), 7.02 (d, J=8.4 Hz, 2H), 5.71 (s, 1H), 2.20 (s, 3H); LC-MS (ESI) (m/z) 481.34.

See general procedure (Example 5) for sulfonylation of 3, followed by hydrogenation and subsequent reaction of intermediate 6 with NaOCN in AcOH.

SBC-110,717: $^1$H-NMR (CD$_3$OD, 400 MHz, δ ppm) 7.60 (d, J=8.8 Hz, 2H), 7.35-7.32 (m, 3H), 7.26-7.16 (m, 5H), 7.10-6.94 (m, 3H), 4.90 (s, 1H), 2.18 (s, 3H); LC-MS (ESI) (m/z) 472.00.

SBC-110,728: $^1$H-NMR (CD$_3$OD, 400 MHz, δ ppm) 7.70 (d, J=8 Hz, 2H), 7.62 (bs, 1H), 7.44 (d, J=8.8 Hz, 2H), 7.36-7.26 (m, 6H), 7.14 (bs, 2H), 5.00 (s, 1H), 2.31 (s, 3H); LC-MS (ESI) (m/z) 517.00.

Example 7

Synthesis of SBC-110,725 and SBC-110,726

Figure 12:
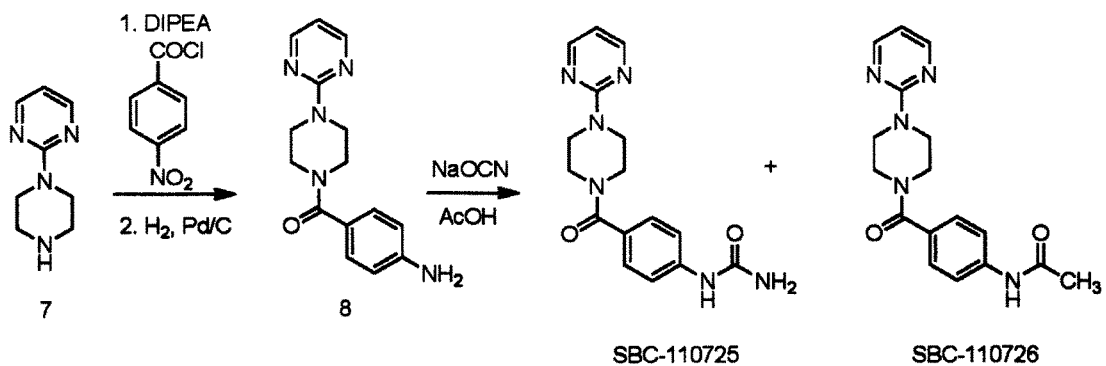
Figure 13:
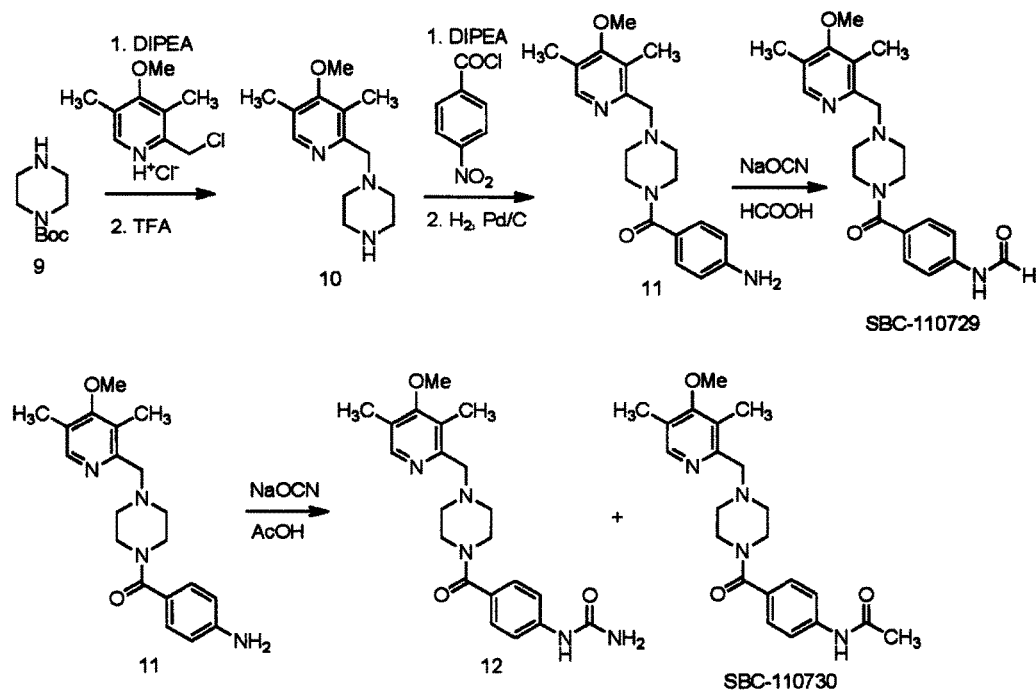

See general procedure (Example 5) for synthesis of intermediate 8 and subsequent reaction with NaOCN in AcOH (FIG. 12).

SBC-110,725: $^1$H-NMR (DMSO-d6, 400 MHz, δ ppm) 8.76 (s, 1H), 8.39 (d, J=4.8 Hz, 2H), 7.47 (d, J=6.8 Hz, 2H), 7.33 (d, J=6.8 Hz, 2H), 6.67 (t, J=4.8 Hz, 1H), 5.94 (s, 2H), 3.57 (bs, 4H), 3.37 (bs, 4H); LC-MS (ESI) (m/z) 327.10.

SBC-110,726: $^1$H-NMR (DMSO-d6, 400 MHz, δ ppm) 10.13 (s, 1H), 8.39 (d, J=4.8 Hz, 2H), 7.65 (d, J=8.4 Hz, 2H), 7.40 (d, J=8.4 Hz, 2H), 6.67 (t, J=4.8 Hz, 1H), 3.78 (bs, 4H), 3.56 (bs, 4H), 2.08 (s, 3H); LC-MS (ESI) (m/z) 326.10.

Example 8

Synthesis of SBC-110,729 and SBC-110,730

Piperazine 10 [1-((4-methoxy-3,5-dimethylpyridin-2-yl)methyl)piperazine] (FIG. 13): Commercially available N-Boc-piperazine (0.40 g, 2.15 mmol), commercially available 2-chloromethyl-4-methoxy-3,5-dimethylpyridine hydrochloride (0.45 g, 2.03 mmol) and triethylamine (0.85 mmol, 6.10 mmol) were stirred overnight at room temperature in dimethylformamide (5 mL). After aqueous workup, dichloromethane extraction and removal of volatiles, the N-Boc protected intermediate was advanced to the next step without further purification. The intermediate was stirred in dichloromethane (5 mL) and trifluoroacetic acid (5 mL) overnight at room temperature. Aqueous work up was followed by addition of concentrated aqueous NaOH solution (8M) which was added dropwise until the pH was adjusted to 7. Ethyl acetate extraction and removal of volatiles afforded crude product 10 (0.44 g, 92% over two steps) which was advanced to the next step without further purification. $^1$H-NMR (CDCl$_3$, 400 MHz, δ ppm) 8.17 (s, 1H), 3.75 (s, 3H), 3.56 (s, 2H), 2.89-2.86 (m, 4H), 2.49-2.43 (m, 4H), 2.30 (s, 3H), 2.23 (s, 3H).

SBC-110,729: Intermediate 11 (0.078 g, 0.2 mmol) was stirred overnight with NaOCN (0.026 g, 0.4 mmol) in formic acid (3 mL). The reaction mixture was transferred to loose silica gel and volatiles were removed. Flash chromatography using a MeOH gradient (0-10%) in dichloromethane afforded SBC-110,729 0.042 g (55%). NMR spectra shows a 2:1 equilibrium between two tautomers: terminal formamide and terminal formimidic acid. $^1$H-NMR (CD$_3$OD, 400 MHz, δ ppm) 8.73 (d, J=11.2 Hz, 1H), 8.36 (d, J=1.6 Hz, 2H), 8.24 (s, 2H), 8.01 (d, J=10.8 Hz, 1H), 7.90 (s, 2H), 7.55 (d, J=8.8 Hz, 4H), 7.41 (d, J=8.4 Hz, 2H), 7.35 (d, J=8.4 Hz, 4H), 7.09 (d, J=8.4 Hz, 2H), 3.80 (s, 12H), 3.68 (s, 8H), 2.60-2.40 (bs, 12H), 2.32 (s, 10H), 2.27 (s, 10H); LC-MS (ESI) (m/z) 383.20.

SBC-110,730: See general procedure (Example 5) for reaction of intermediate 11 and NaOCN in AcOH. $^1$H-NMR (CDCl$_3$, 400 MHz, δ ppm) 8.20 (s, 1H), 7.58 (bs, 1H), 7.49 (d, J=8 Hz, 2H), 7.34 (d, J=8.4 Hz, 2H), 3.77 (s, 3H), 3.64 (s, 3H), 2.49 (bs, 4H), 2.31 (s, 3H), 2.25 (s, 3H), 2.17 (s, 3H), 2.08 (s, 2H); LC-MS (ESI) (m/z) 397.20.

Example 9

Synthesis of SBC-110,733-6, SBC-110,769, and SBC-110,771

1-(3-Chloro-4-methylphenyl)-3-phenylpiperazine (compound of type 14, FIG. 11): 2-phenyl-piperazine (0.13 g, 0.80 mmol), 2-Cl-4-Br-toluene (0.10 mL, 0.76 mmol), Pd$_2$dba$_3$ (0.07 g, 0.08 mmol), BINAP (0.048 g, 0.08 mmol) and KOtBu (0.13 g, 1.14 mmol) were stirred in toluene (2 mL) at 80° C. Aqueous work up, dichloromethane extraction and removal of volatiles was followed by flash chromatography separation using ethyl acetate gradient (10-60%) in hexanes to afford 0.13 g (56%) of 1-(3-Chloro-4-methylphenyl)-3-phenylpiperazine 14. $^1$H-NMR (CDCl$_3$, 400 MHz, δ ppm) 7.46-7.44 (m, 2H), 7.39-7.29 (m, 3H), 7.08 (d, J=8.4 Hz, 1H), 6.91 (d, J=2.8 Hz, 1H), 6.75 (dd, J=8.8, 2.8 Hz, 1H), 3.96 (dd, J=10.4, 2.8 Hz, 1H), 3.57-3.54 (m, 2H), 3.24 (dt, J=11.6, 3.2 Hz, 1H), 2.86 (td, J=11.6, 3.2 Hz, 1H), 2.68 (t, J=11.2 Hz, 1H), 2.27 (s, 3H).

See general procedure (Example 5) for reaction of intermediates 15 and 16 with NaOCN in AcOH.

SBC-110,733: $^1$H-NMR (CDCl$_3$, 400 MHz, δ ppm) 7.91 (s, 1H), 7.30 (bs, 2H), 7.19 (t, J=7.4 Hz, 2H), 7.13-7-08 (m, 4H), 6.99-6.94 (m, 3H), 6.75 (d, J=2.4 Hz, 1H), 6.58 (dd, J=8.4, 2.4 Hz, 1H), 4.95 (bs, 2H), 3.92 (d, J=12.4 Hz, 1H), 3.32-3.21 (m, 2H), 3.06 (dd, J=12.8, 3.6 Hz, 1H), 2.72 (t, J=10.4 Hz, 1H), 2.12 (s, 3H); LC-MS (ESI) (m/z) 449.10.

SBC-110,734: $^1$H-NMR (CD$_3$OD, 400 MHz, δ ppm) 8.48 (s, 1H), 7.45 (bs, 2H), 7.42 (d, J=8.4 Hz, 2H), 7.35-7.29 (m, 4H), 7.23-7-19 (m, 1H), 7.00 (d, J=8.4 Hz, 2H), 6.83 (d, J=8.4 Hz, 2H), 4.51 (s, 1H), 4.14 (d, J=12.4 Hz, 1H), 3.87-3.84 (m, 1H), 3.45-3.41 (m, 1H), 3.10 (dd, J=12.8, 4 Hz, 1H), 2.78 (td, J=11.8, 3.2 Hz, 1H), 2.18 (s, 3H); LC-MS (ESI) (m/z) 415.20.

SBC-110,735: $^1$H-NMR (CDCl$_3$, 400 MHz, δ ppm) 8.00 (bs, 1H), 7.45-7.35 (m, 4H), 7.30-7.20 (m, 5H), 7.04 (d, J=8.4 Hz, 1H), 6.85 (d, J=2.4 Hz, 1H), 6.68 (dd, J=8.4, 2.4 Hz, 1H), 403 (d, =12.4 Hz, 1H), 3.37 (d, i=10.8 Hz, 1H), 3.27 (t, J=11.8 Hz, 1H), 3.13 (dd, J=12.4 Hz, 111), 2.79 (t, J=10.2 Hz, 1H), 2.21 (s, 3H), 2.07 (s 3H); LC-MS (ESI) (m/z) 448.15.

SBC-110,736: $^1$H-NMR (CDCl$_3$, 400 MHz, δ ppm) 7-56-7.50 (m, 4H), 7.41-7.28 (m, 5H), 7.11 (d, J=8 Hz, 2H), 6.88 (d, J=8.4 Hz, 2H), 4.14 (d, J=12.4 Hz, 1H), 3.45 (d, J=11.2 Hz, 1H), 3.35 (t, J=12.4 Hz, 1H), 3.19 (dd, J=12.8, 4 Hz, 1H), 2.86 (t, J=11 Hz, 1H), 2.29 (s, 3H), 2.18 (s, 3H); LC-MS (ESI) (m/z) 414.20.

SBC-110,769: $^1$H-NMR (DMSO-d6, 400 MHz, δ ppm) 10.12 (s, 1H), 7.95 (d, J=8.4 Hz, 1H), 7.80-7.60 (m, 3H), 7.55-7.25 (m, 11H), 7.15 (d, J=7.6 Hz, 1H), 3.81-3.79 (m, 2H), 2.87-2.84 (m, 1H), 2.58 (s, 3H), 2.06 (s, 3H); LC-MS (ESI) (m/z) 464.20.

SBC-110,771: $^1$H-NMR (DMSO-d6, 400 MHz, δ ppm) 9.06 (s, 1H), 7.92 (d, J=8 Hz, 1H), 7.70-7.66 (m, 3H), 7.59 (d, J=8.8 Hz, 2H), 7.53-7.46 (m, 3H), 7.37 (t, J=7.4 Hz, 2H), 7.30 (t, J=7.6 Hz, 2H), 7.23 (d, J=7.6 Hz, 1H), 6.90 (d, J=7.6 Hz, 1H), 6.10 (s, 2H), 3.82 (d, J=13.6 Hz, 1H), 3.61 (t, J=11.4 Hz, 1H), 3.52 (d, J=12 Hz, 1H), 3.09 (d, J=12.4 Hz, 1H), 2.98 (dd, J=12, 4 Hz, 1H), 2.54 (s, 3H), 2.45 (t, J=1.8 Hz, 1H); LC-MS (ESI) (m/z) 500.10.

Example 10

Test for Efficacy in Animal Model

SBC-110,686, SBC-110,733 and SBC-110,736 were tested for their efficacy in male mice (C57BL/6 mice). Mice were housed as four animals per cage under climate-controlled conditions of temperature (20-24° C.), humidity (60-70%), and alternating 12 h light/dark cycles. The mice were divided into five groups as shown in FIG. 14. One group was fed commercial chow diet (Prolab RMH 3000, PMI feeds, St. Louis, Mo.) to serve as a negative control, while the other four groups were fed high fat diet (TD.06414), which provides 60% of calories from fat. Water was provided ad libitum. Plasma was collected once weekly to monitor the level of LDL. After 4 weeks of feeding a high fat diet, mice were randomly assigned to one of several groups such that the average LDL levels were equal among different groups. One of the four groups of mice fed high fat diet was treated with vehicle and served as a positive control, whereas each of the other three groups was treated daily with 8 mg/kg of one of the compounds subcutaneously for two weeks. Blood samples (75 μl) were collected twice weekly after drug administration from the retro-orbital venous plexus via heparinized capillary tubes containing 2 USP units of ammonium heparin per tube (Carolina, Burlington, N.C.). Plasma were separated immediately by centrifugation (5,000×g) for 5 min at room temperature and then kept at −80° C. until assayed for lipid profile. Plasma cholesterol, LDL-C, HDL-C, and triglyceride levels were measured enzymatically. Additionally, the plasma levels of PCSK9 and chemokines/cytokines were measured for potential pleiotropic effects of PCSK9 inhibitors using ELISA and multiplex assays.

Figure 15:
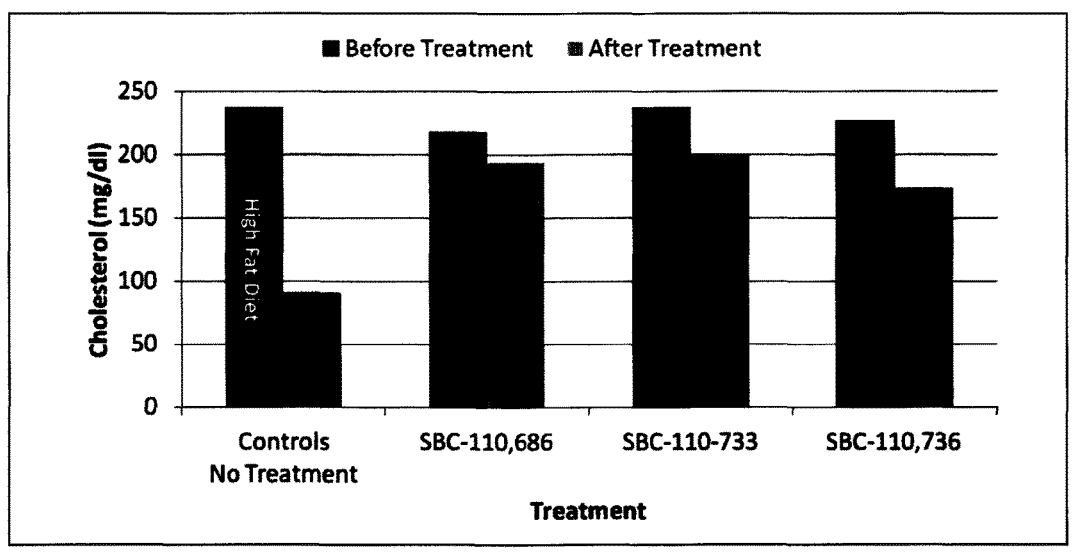
FIG. 15 shows the effect of compounds on total cholesterol (mg/dl) levels in mice fed high fat diet compared to the control mice.
Figure 16:
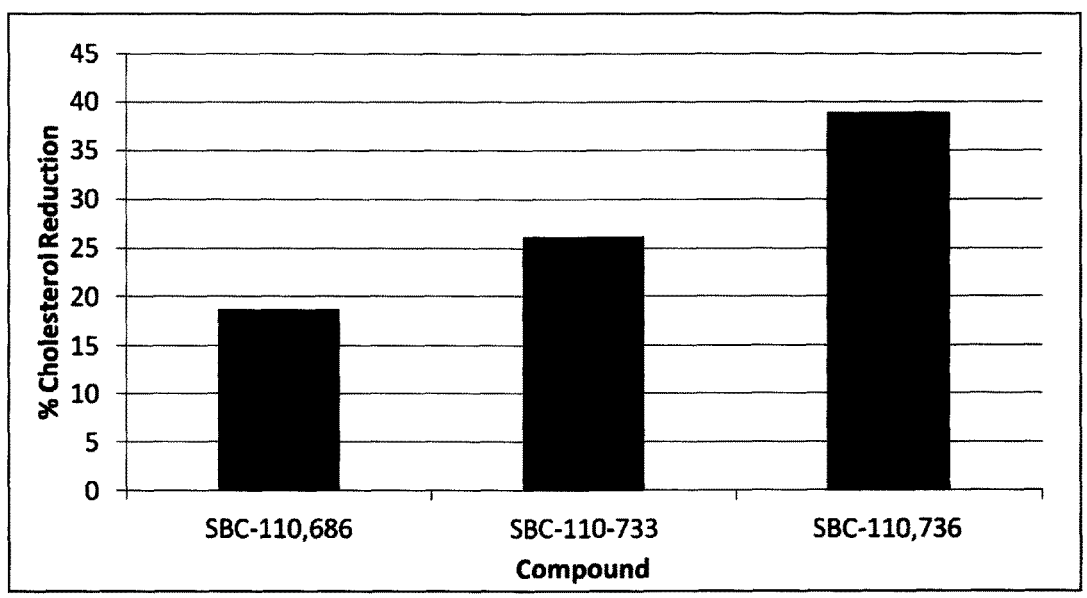
FIG. 16 shows the percent reduction in total cholesterol levels ranging from 18 to 38% when mice fed high fat diet are treated with compounds and compared to the control mice fed high fat diet.

Our data demonstrated that SBC-110,686, SBC-110,733 and SBC-110,736 lowered cholesterol levels in mice that were fed high fat diet (FIGS. 15 and 16), with SBC-110,736 showing a mean of 38% reduction (P<0.01) in total cholesterol levels after two weeks relative to high fat diet animal levels and a mean 50% reduction (P<0.01) toward return to regular diet cholesterol levels.

Figure 17:
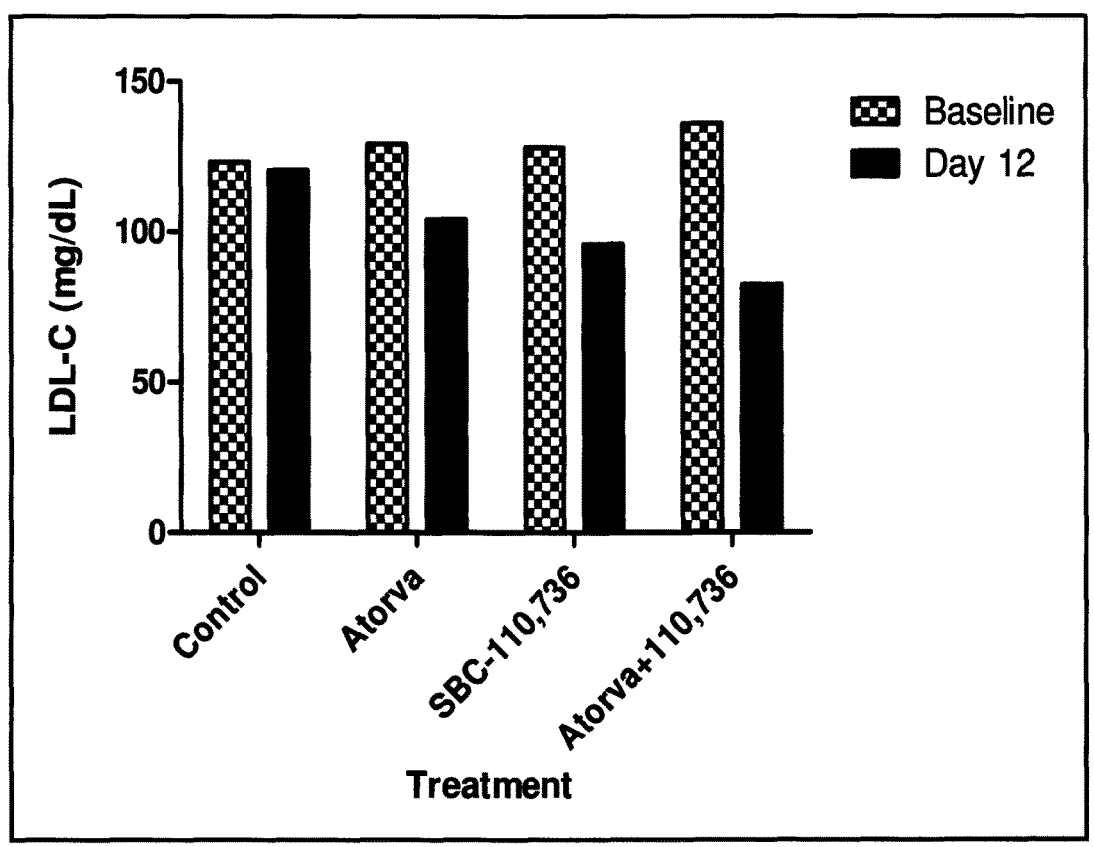
FIG. 17 shows the effect of combinations of atorvastatin and SBC-110,736 on plasma LDL-C in mice fed high fat diet.

A second study was conducted with atorvastatin. Data demonstrated that the compounds in combination with atorvastatin resulted in an additive effect on lowering LDL-C levels in mice fed high fat diet. FIG. 17 shows data obtained from SBC-110,736 in combination with atorvastatin in mice, indicating an additive effect of reduction in LDL-C level after two weeks of treatments.

The foregoing specification includes citations to certain publications, which are provided to indicate the state of the art to which this invention pertains. The entire disclosure of each of the cited publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the appended claims. Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed invention. All compositions and methods of use thereof that embody the present invention can, in alternate embodiments, be more specifically defined by any of the transitional terms "comprising", "consisting essentially of" and "consisting of".

REFERENCES

1. Grundy S M, Cleeman J I, Merz C N B, Brewer, Jr, H B, Clark L T, Hunninghake D B, Pasternak R C, Smith, Jr, S C, Stone N J (2004). Implications of Recent Clinical Trials for the National Cholesterol Education Program Adult Treatment Panel III Guidelines. *Circulation* 110, 227-239.
2. Abifadel M, Varret M, Rabès J, Allard D, Ouguerram K, Devillers M, Cruaud C, Benjannet S, Wickham L, Erlich D, Derré A, Villéger L, Farnier M, Beucler I, Bruckert E, Chambaz J, Chanu B, Lecerf J, Luc G, Moulin P, Weissenbach J, Prat A, Krempf M, Junien C, Seidah N, Boileau C (2003). Mutations in PCSK9 cause autosomal dominant hypercholesterolemia. *Nat. Genet* 34, 154-156.
3. Pisciotta L, Priore Oliva C, Cefalu A B, Noto D, Bellocchio A, Fresa R, Cantafora A, Patel D, Averna M, Tarugi P, Calandra S, Bertolini S (2006). Additive effect of mutations in LDLR and PCSK9 genes on the phenotype of familial hypercholesterolemia. *Atherosclerosis* 186, 433-440.
4. Maxwell K, Breslow J (2004). Adenoviral-mediated expression of PCSK9 in mice results in a low-density lipoprotein receptor knockout phenotype. *Proc Natl Acad Sci USA* 101, 7100-7105.
5. Benjannet S, Rhainds D, Essalmani R, Mayne J, Wickham L, Jin W, Asselin M, Hamelin J, Varret M, Allard D, Trillard M, Abifadel M, Tebon A, Attie A D, Rader D J, Boileau C, Brissette L, Chrétien M, Prat A, Seidah N G (2004). NARC-1/PCSK9 and its natural mutants: zymogen cleavage and effects on the low density lipoprotein (LDL) receptor and LDL cholesterol. *J Biol Chem* 279, 48865-48875.
6. Cohen J, Pertsemlidis A, Kotowski I, Graham R, Garcia C, Hobbs H (2005). Low LDL cholesterol in individuals of African descent resulting from frequent nonsense mutations in PCSK9. *Nature Genetics* 37, 161-165.
7. Rashid S, Curtis D, Garuti R, Anderson N, Bashmakov Y, Ho Y, Hammer H, Moon Y, Horton J (2005). Decreased plasma cholesterol and hypersensitivity to statins in mice lacking PCSK9. *Proc Natl Acad Sci USA* 102, 5374-5379.
8. Zhao Z, Tuakli-Wosornu Y, Lagace T, Kinch L, Grishin N, Horton J, Cohen J, Hobbs H (2006). Molecular Characterization of Loss-of-Function Mutations in PCSK9 and Identification of a Compound Heterozygote. *Am J Human Genetics* 79, 514-523.
9. Benjannet S, Rhainds D, Hamelin J, Nassoury N, Seidah N G (2006). The proprotein convertase PCSK9 is inactivated by furin and/or PC5/6A: functional consequences of natural mutations and post-translational modifications. *J Biol Chem* 281, 30561-30572.

10. Li J, Tumanut C, Gavigan J-A, Huang W-J, Hampton E N, Tumanut R, Suen K F, Trauger J W, Spraggon G, Lesley S A, Liau G, Yowe D, Harris J L (2007). Secreted PCSK9 promotes LDL receptor degradation independently of proteolytic activity. *Biochem J* 406, 203-207.
11. McNutt M C, Lagace T A, Horton J D (2007). Catalytic activity is not required for secreted PCSK9 to reduce low density lipoprotein receptors in HepG2 cells. *J Biol Chem* 282, 20799-20803.
12. Zhang D-W, Lagace T A, Garuti R, Zhao Z, McDonald M, Horton J D, Cohen J C, Hobbs H H (2007). Binding of proprotein convertase subtilisin/kexin type 9 to epidermal growth factor-like repeat A of low density lipoprotein receptor decreases receptor recycling and increases degradation. *J Biol Chem* 282, 18602-18612.
13. Kwon H J, Lagace T A, McNutt M C, Jay D. Horton J D, Deisenhofer J (2008). Molecular basis for LDL receptor recognition by PCSK9. *Proc Natl Acad Sci USA* 105, 1820-5.
14. Bottomley M J, Cirillo A, Orsatti L, Ruggeri L, Fisher T S, Santoro J C, Cummings R T, Cubbon R M, Lo Surdo P, Calzetta A, Noto A, Baysarowich J, Mattu M, Talamo F, De Francesco R, Sparrow C P, Sitlani A, Carfí A (2009). Structural and biochemical characterization of the wild type PCSK9/EGF(AB) complex and natural familial hypercholesterolemia mutants. *J Biol Chem* 284, 1313-1323.
15. Seidah N G (2009). PCSK9 as a therapeutic target of dyslipidemia. *Expert Opin Ther Targets* 13, 19-28.
16. Graham M J, Lemonidis K M, Whipple C P, Subramaniam A, Monia B P, Crooke S T, Crooke R M (2007). Antisense inhibition of proprotein convertase subtilisin/kexin type 9 reduces serum LDL in hyperlipidemic mice. *J Lipid Res* 48, 763-767.
17. Frank-Kamenetsky M, Grefhorst A, Anderson N N, Racie T S, Bramlage B, Akinc A, Butler D, Charisse K, Dorkin R, Fan Y, Gamba-Vitalo C, Hadwiger P, Jayaraman M, John M, Jayaprakash K N, Maier M, Nechev L, Rajeev K G, Read T, Röhl I, Soutschek J, Tan P, Wong J, Wang G, Zimmermann T, de Fougerolles A, Vornlocher H P, Langer R, Anderson D G, Manoharan M, Koteliansky V, Horton J D, Fitzgerald K (2008). Therapeutic RNAi targeting PCSK9 acutely lowers plasma cholesterol in rodents and LDL cholesterol in nonhuman primates. *Proc Natl Acad Sci USA* 105, 11915-11920.
18. Piper D, Jackson S, Liu Q, Romanow W, Shetterly S, Thibault S, Shan B, Walker N (2007). The Crystal Structure of PCSK9: A Regulator of Plasma LDL-Cholesterol. *Structure* 15, 545-552.
19. Cunningham D, Danley D E, Geoghegan K F, Matthew C Griffor M C, Hawkins J L, Subashi T A, Varghese A H, Ammirati M J, Culp J S, Hoth L R, Mansour M N, McGrath K M, Seddon A P, Shenolikar S, Stutzman-Engwall K J, Warren L C, Xia D, Qiu X (2007). Structural and biophysical studies of PCSK9 and its mutants linked to familial hypercholesterolemia. *Nature Struc Mol Biol* 14, 413-419.
20. Seidah N, Benjannet S, Wickham L, Marcinkiewicz J, Jasmin S, Stifani S, Basak A, Prat A, Chrétien M (2003). The secretory proprotein convertase neural apoptosis-regulated convertase 1 (NARC-1) liver regeneration and neuronal differentiation. *Proc Natl Acad Sci USA* 100, 928-933.
21. McNutt M C, Kwon H J, Chen C, Chen J R, Horton J D, Lagace T A (2009). Antagonism of secreted PCSK9 increases low density lipoprotein receptor expression in HepG2 cells. *J Biol Chem* 284, 10561-10570.
22. Swergold G, Biedermann S, Renard R, Nadler D, Wu R; Mellis S (2010). Safety, Lipid, and Lipoprotein Effects of REGN727/SAR236553, a Fully-Human Proprotein Convertase Subtilisin Kexin 9 (PCSK9) Monoclonal Antibody Administered Intravenously to Healthy Volunteers. *Circulation* 122, A23251.
23. Dias C, Shaywitz A, Smith B, Emery M, Bing G, Gibbs J, Wishner B, Stolman D, Crispino C, Cook B, Colbert A, Retter M, Xu R (2011). A Phase 1, Randomized, Double-Blind, Placebo-Controlled, Ascending Single Dose Study to Evaluate the Safety, Tolerability and Pharmacodynamics of AMG145. *Circulation* 124.
24. Amgen (2010) Ascending Multiple Dose Study to Evaluate the Safety, Tolerability, Pharmacokinetics and Pharmacodynamics of AMG 145 in Subjects With Hyperlipidemia on Stable Doses of a Statin. ClinicalTrails.Gov
25. Crunkhorn S (2012). PCSK9 antibody reduces LDL cholesterol. *Nature Rev Drug Disc* 11, 11.

What is claimed is:

1. A composition comprising:

A) a compound represented by the formula:

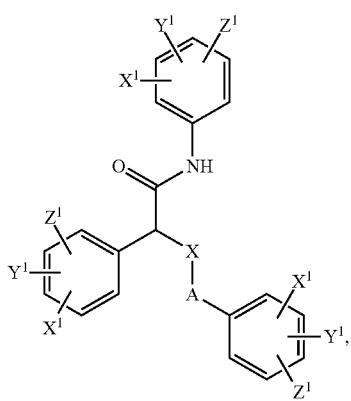

(II)

including the pharmaceutically acceptable salts and all stereoisomers thereof, wherein $X^1$, $Y^1$, and $Z^1$ are the same or different and each represents hydrogen or a substituent selected from the group consisting of hydroxyl, halogen, amino, alkoxy, carboxy, amido, aminocarbonylamino, monoalkylaminocarbonylamino, dialkylaminocarbonylamino, carbamato, carboxamido, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinyl and, optionally substituted, lower alkyl, alkenyl, alkynyl, cycloalkyl, aryl, heterocycle, and heteroaryl;

X is O or $NR^4$; $R^4$ is selected from the group consisting of H and lower alkyl;

A is CO, $CONR^5$, or $SO_2$; $R^5$ is selected from the group consisting of H and lower alkyl, and B) a low density lipoprotein (LDL) lowering drug.

2. A compound which is N-(3-chloro-4-methylphenyl)-2-[(4-acetamidophenyl)formamido]-2-phenylacetamide.

3. A compound which is [(3-chloro-4-methylphenyl)carbamoyl](phenyl)methyl 4-acetamidobenzoate.

4. The composition of claim 1, wherein said LDL lowering drug is a statin.

5. The composition of claim 1, wherein said LDL lowering drug is atorvastatin.

6. The composition of claim 1, wherein said amido is a formamido, alkylamido, or arylamido.

* * * * *

SEQUENCE LISTING

```
<160> NUMBER OF SEQ ID NOS: 1

<210> SEQ ID NO 1
<211> LENGTH: 692
<212> TYPE: PRT
<213> ORGANISM: Homo Sapiens

<400> SEQUENCE: 1

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80
```

-continued

```
Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
```

```
                 500                 505                 510
Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
        530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
        610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
                660                 665                 670

Thr Ala Val Ala Ile Cys Cys Arg Ser Arg His Leu Ala Gln Ala Ser
            675                 680                 685

Gln Glu Leu Gln
            690
```